(12) United States Patent
Kong et al.

(10) Patent No.: US 9,963,518 B2
(45) Date of Patent: May 8, 2018

(54) CYCLIC OLIGOSACCHARIDES FOR USE IN THE TREATMENT AND PREVENTION OF BACTERIAL INFECTION

(75) Inventors: Lingbing Kong, Oxford (GB); Benjamin G. Davis, Oxford (GB); Hagan Bayley, Oxford (GB)

(73) Assignee: Oxford University Innovation Limited, Oxford (GB)

( * ) Notice: Subject to any disclaimer, the term of this patent is extended or adjusted under 35 U.S.C. 154(b) by 0 days. days.

(21) Appl. No.: 14/239,826

(22) PCT Filed: Aug. 20, 2012

(86) PCT No.: PCT/GB2012/052029
§ 371 (c)(1),
(2), (4) Date: Jun. 17, 2014

(87) PCT Pub. No.: WO2013/027040
PCT Pub. Date: Feb. 28, 2013

(65) Prior Publication Data
US 2014/0296180 A1   Oct. 2, 2014

(30) Foreign Application Priority Data

Aug. 22, 2011  (GB) .................................. 1114459.9

(51) Int. Cl.
*A61K 31/724* (2006.01)
*C08B 37/16* (2006.01)
*A01N 43/16* (2006.01)
*A61K 47/40* (2006.01)

(52) U.S. Cl.
CPC .......... *C08B 37/0012* (2013.01); *A01N 43/16* (2013.01); *A61K 31/724* (2013.01); *A61K 47/40* (2013.01)

(58) Field of Classification Search
None
See application file for complete search history.

(56) References Cited

U.S. PATENT DOCUMENTS

| | | | | |
|---|---|---|---|---|
| 5,241,059 A * | 8/1993 | Yoshinaga | .......... | C08B 37/0012 127/32 |
| 2005/0222085 A1* | 10/2005 | Kis | ....................... | A61K 31/724 514/58 |
| 2006/0199785 A1 | 9/2006 | Fahmi et al. | | |
| 2011/0207764 A1* | 8/2011 | Alakhov | .............. | A61K 9/0019 514/283 |

FOREIGN PATENT DOCUMENTS

| | | |
|---|---|---|
| EP | 1 747 785 A1 | 1/2007 |
| JP | S52138580 A | 11/1977 |
| JP | S5319392 A | 2/1978 |
| WO | 03/063882 A1 | 8/2003 |
| WO | 2006/075580 A1 | 7/2006 |
| WO | 2006/083678 A2 | 8/2006 |
| WO | 2008/044075 A1 | 4/2008 |
| WO | 2008/116194 A2 | 9/2008 |
| WO | 2009/058327 A1 | 5/2009 |
| WO | 2010/148191 A2 | 12/2010 |

OTHER PUBLICATIONS

Ragle, B. et al "Prevention and treatment of *Staphylococcus aureus* . . . " Antimicrob. Agents Chemother. (2010) vol. 54, No. 1, pp. 298-304.*
Yannakopoulou, K. et al "Symmetry requirements for effective blocking . . . " Antimicrob. Agents Chemother. (2011) vol. 55, No. 7, pp. 3594-3597.*
Ericsson, D. et al "Wzy-dependent bacterial capsules as potential drug targets" Curr. Drug Targets (2012) vol. 13, pp. 1421-1431.*
Ashton, Peter R. et al., "Amino Acid Derivatives of β-Cyclodextrin," *J. Org. Chem.* (1996), 61(3):903-908.
Astier, Yann et al., "Toward Single Molecule DNA Sequencing: Direct Identification of Ribonucleoside and Deoxyribonucleoside 5'-Monophosphates by Using an Engineered Protein Nanopore Equipped with a Molecular Adapter," *J. Am. Chem. Soc.* (2006), 128(5):1705-1710.
Banerjee, Arijit et al., "Molecular bases of cyclodextrin adapter interactions with engineered protein nanopores," *PNAS* (May 4, 2010), 107(18):8165-8170.
Bayley, Hagan et al., "Droplet interface bilayers," *Mol. BioSyst.* (2008), 4:1191-1208.
Brisson, Jean-Robert et al., "Helical Epitope of the Group B Meningococcal α(2-8)-Linked Sialic Acid Polysaccharide," *Biochemistry* (1992), 31(21):4996-5004.
Brisson, Jean-Robert et al., "NMR and Molecular Dynamics Studies of the Conformational Epitope of the Type III Group B *Streptococcus* Capsular Polysaccharide and Derivatives," *Biochemistry* (1997), 36(11):3278-3292.
Casas-Solvas, Juan M. et al., "Synthesis of Nitrogen-Functionalized β-Cycloaltrins," *J. Org. Chem.* (2004), 69(25):8942-8945.
Chakraborty, Ajit K. et al., "Primary Structure of the *Eschericia coli* Serotype K30 Capsular Polysaccharide," *Journal of Bacteriology* (Feb. 1980), 141(2):971-972.
Clarke, Bradley R. et al., "Nonreducing Terminal Modifications Determine the Chain Length of Polymannose O Antigens of *Escherichia coli* and Couple Chain Termination to Polymer Export via an ATP-binding Cassette Transporter," *The Journal of Biological Chemistry* (Aug. 20, 2004), 279(34):35709-35718.
Cuthbertson, Leslie et al., "Pivotal Roles of the Outer Membrane Polysaccharide Export and Polysaccharide Copolymerase Protein Families in Export of Extracellular Polysaccharides in Gram-Negative Bacteria," *Microbiology and Molecular Biology Reviews* (Mar. 2009), 73(1):155-177.

(Continued)

*Primary Examiner* — Leigh C Maier
(74) *Attorney, Agent, or Firm* — Kilpatrick Townsend & Stockton LLP

(57) ABSTRACT

Compounds which inhibit Wza-mediated polysaccharide transport are useful in the prevention or treatment of bacterial infection, in particular of *E. coli* infection. The compounds are typically cyclic oligosaccharides such as cyclodextrins, which bear positively charged functional groups at the primary carbon position.

11 Claims, 6 Drawing Sheets

(56) References Cited

OTHER PUBLICATIONS

Domenico, Philip et al., Surface Antigen Exposure by Bismuth Dimercaprol Suppression of *Klebsiella pneumonia* Capsular Polysaccharide, *Infection and Immunity* (Feb. 1999), 67(2):664-669.
Dong, Changjiang et al., "Wza the translocon for *E. coli* capsular polysaccharides defines a new class of membrane protein," *Nature* (Nov. 2006), 444:226-229.
Drummelsmith, Jolyne et al., "Translocation of group 1 capsular polysaccharide to the surface of *Escherichia coli* requires a multimeric complex in the outer membrane," *The EMBO Journal* (2000), 19(1):57-66.
Engeldinger, Eric et al., "Capped Cyclodextrins," *Chemical Reviews* (2003), 103(11):4147-4173.
Fernandez-Prada, Carmen M. et al., "Deletion of wboA Enhances Activation of the Lectin Pathway of Complement in *Brucella abortus* and *Brucella melitensis*," *Infection and Immunity* (Jul. 2001), 69(7):4407-4416.
Gattuso, Giuseppe et al., "Synthetic Cyclic Oligosaccharides," *Chem. Rev.* (1998), 98(5):1919-1958.
Gu, Li-Qun et al., "Stochastic sensing of organic analytes by a pore-forming protein containing a molecular adapter," *Nature* (Apr. 22, 1999), 398:686-690.
Gu, Li-Qun et al., Interaction of the Noncovalent Molecular Adapter, β-Cyclodextrin, with the Staphylococcal α-Hemolysin Pore, *Biophysical Journal* (Oct. 2000), 79(4):1967-1975.
Howard, C.J. et al., "The Virulence for mice of Strains of *Escherichia coli* related to the Effects of K Antigens on their Resistance to Phagocytosis and Killing by Complement," *Immunology* (1971) 20:767-777.
Hungerer, D. et al., "Immunochemistry of K Antigens of *Escherichia coli,*" *European J. Biochem.* (1967) 2:115-126.
Infectious Diseases Society of America (IDSA), *Bad Bugs, No Drugs, As Antibiotic Discovery Stagnates . . . A Public Health Crisis Brews*, (Jul. 2004), 36 pages.
Ishihara, Keiko et al., "Low-affinity spermine block mediating outward currents through Kir2.1 and Kir2.2 inward rectifier potassium channels," *J. Physiol.* (2007) 583(3):891-908.
Jordt, Sven-Eric et al., "Acid potentiation of the capsaicin receptor determined by a key extracellular site," *PNAS* (Jul. 5, 2000), 97(14)8134-8139.
Jung, Kirsten et al., "K+ and Ionic Strength Directly Influence the Autophosphorylation Activity of the Putative Turgor Sensor KdpD of *Eschericia coli,*" *The Journal of Biological Chemistry* (Dec. 22, 2000), 275(51):40142-40147.
Kamal, Ahmed et al., "Synthesis of Cyclodextrin Derivatives of Amino-(thiazolyl) Coumarins as Potential Antimicrobial Agents," *Letters in Drug Design & Discovery* (2010) 7(9):665-673.
Karginov, Vladimir A. et al., "Search for Cyclodextrin-Based Inhibitors of Anthrax Toxins: Synthesis, Structural Features, and Relative Activities," *Antimicrobial Agents and Chemotherapy* (Nov. 2006), 50(11):3740-3753.
Karginov, Vladimir A. et al., "β-Cyclodextrin derivatives that inhibit anthrax lethal toxin," *Bioorg. Med. Chem.* (2006) 14:33-40.
Karginov, Vladimir A. et al., "Inhibition of *S. aureus* α-hemolysin and *B. anthracis* lethal toxin by β-cyclodextrin derivatives," *Bioorganic & Medicinal Chemistry* (2007) 15:5424-5431.
Keo, Thormika et al., "Campylobacter capsule and lipooligosaccharide confer resistance to serum and cationic antimicrobials," *Virulence* (Jan./Feb. 2011), 2(1):30-40.
Kolkman, Marc A. B. et al., "Functional Analysis of Glycosyltransferases Encoded by the Capsular Polysaccharide Biosynthesis Locus of *Streptococcus pneumoniae* Serotype 14," *The Journal of Biological Chemistry* (Aug. 1, 1997), 272(31):19502-19508.
Lazarev, V. N. et al., "Antimicrobial Peptides and Their Use in Medicine," *Applied Biochemistry and Microbiology* (2010) 46(9):803-814.
Lebeer, Sarah et al., "Host interactions of probiotic bacterial surface molecules: comparison with commensals and pathogens," *Nature Reviews Microbiology* (Mar. 2010), 8:171-184.
Llobet, Enrique et al., "Capsule polysaccharide is a bacterial decoy for antimicrobial peptides," *Microbiology* (2008) 154:3877-3886.
Merzlyak, Petr G. et al., "Conductance and Ion Selectivity of a Mesoscopic Protein Nanopore Probed with Cysteine Scanning Mutagensis," *Biophysical Journal* (Nov. 2005), 89(5):3059-3070.
Miles, George et al., "Subunit composition of a bicomponent toxin: Staphylococcal leukocidin forms an octameric transmembrane pore," *Protein Science* (2002), 11:894-902.
Moranta, David et al., "*Klebsiella pneumonia* Capsule Polysaccharide Impedes the Expression of β-Defensins by Airway Epithelial Cells," Infection and Immunity (Mar. 2010), 78(3):1135-1146.
Nikaido, Hiroshi, "Molecular Basis of Bacterial Outer Membrane Permeability Revisited," *Microbiology and Molecular Biology Reviews* (Dec. 2003), 67(4):593-656.
Pearl, Mirilee et al., "Studies on the Spectrin-like Protein from the Intestinal Brush Border, TW 260/240, and Characterization of Its Interaction with the Cytoskeleton and Actin," *The Journal of Cell Biology* (Jan. 1984), 98:66-78.
Regueiro, Veronica et al., "*Klebsiella pneumonia* Increases the Levels of Toll-Like Receptors 2 and 4 in Human Airway Epithelial Cells," *Infection and Immunity* (Feb. 2009), 77(2):714-724.
Sali, Andrej et al., "Comparative Protein Modelling by Satisfaction of Spatial Restraints," *J. Mol. Biol.* (1993) 234:779-815.
Sen, Keya et al., "Porin Channels in Intact Cells of *Escherichia coli* Are Not Affected by Donnan Potentials Across the Outer Membrane," *The Journal of Biological Chemistry* (Jan. 25, 1988), 263(3):1182-1187.
Smart, Oliver S. et al., "The Pore Dimensions of Gramicidin A," *Biophysical Journal* (Dec. 1993) 65:2455-2460.
Stauffer, David A. et al., "Electrostatic Potential of the Acetylcholine Binding Sites in the Nicotinic Receptor Probed by Reactions of Binding-Site Cysteines with Charged Methanethiosulfonates," *Biochemistry* (1994) 33(22):6840-6849.
Stukalov, Oleg et al., "Use of Atomic Force Microscopy and Transmission Electron Microscopy for Correlative Studies of Bacterial Capsules," *Applied and Environmental Microbiology* (Sep. 2008), 74(17):5457-5465.
Walker, Barbara et al., "Functional Expression of the α-Hemolysin of *Staphylococcus aureus* in Intact *Escherichia coli* and in Cell Lysates," *The Journal of Biological Chemistry* (May 25, 1992), 267(15):10902-10909.
Wenz, Gerhard et al., "Cyclodextrin Rotaxanes and Polyrotaxanes," *Chem. Rev.* (2006) 106(3):782-817.
Whitfield, Chris et al., "Mutants of *Eschericihia coli* O9:K30 with Altered Synthesis and Expression of the Capsular K30 Antigen," *Journal of General Microbiology* (1989) 135:2589-2599.
Whitfield, Chris, "Biosynthesis and Assembly of Capsular Polysaccharides in *Escherichia coli,*" *Annu. Rev. Biochem.* (2006) 75:39-68.
Wilson, R. Paul et al., "The Vi Capsular Polysaccharide Prevents Complement Receptor 3-Mediated Clearance of *Salmonella enterica* Serotype Typhi," *Infection and Immunity* (Feb. 2011), 79(2):830-837.
Woodhull, Ann M., "Ionic Blockage of Sodium Channels in Nerve," *The Journal of General Physiology* (1973) 61:687-708.
Wu, Chieh-Liang et al., "Subinhibitory Bismuth-Thiols Reduce Virulence of *Pseudomonas aeruginosa,*" *American Journal of Respiratory Cell and Molecular Biology* (2002) 26:731-738.
Wu-Hai-Chen et al., "Protein Nanopores with Covalently Attached Molecular Adapters," *J. Am. Chem. Soc.* (2007) 129(51):16142-16148.
Xiao, Botao et al., Modulation of HU-DNA interactions by salt concentration and applied force, *Nucleic Acids Research* (2010) 38(18):6176-6185.

* cited by examiner

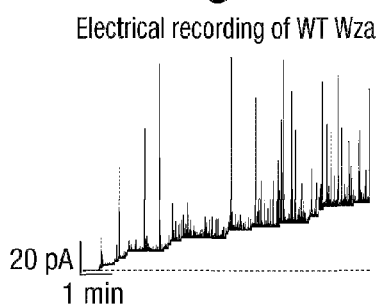
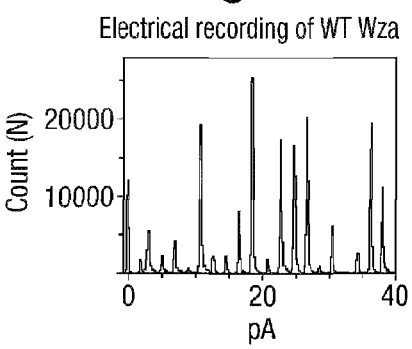
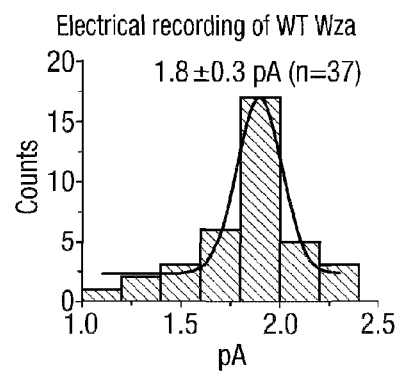
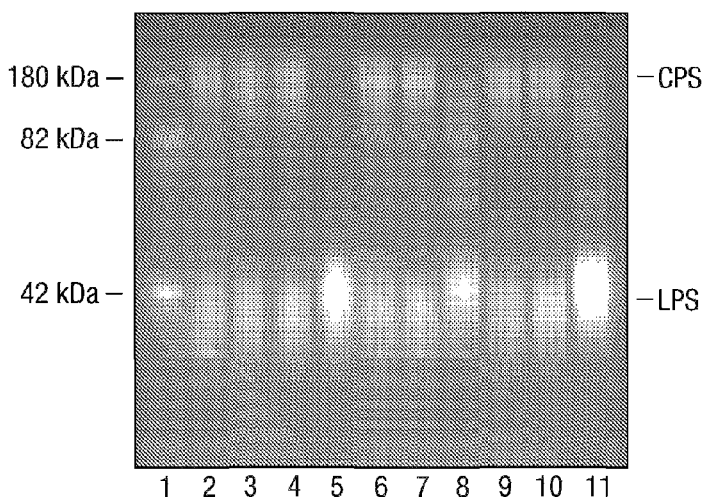

Effect of various concentrations of am₈γCD on CPS and LPS transports in E. coli E69

Effect of various concentrations of am₈γCD on CPS and LPS transports in E. coli E69

Effect of various concentrations of am₈γCD on CPS and LPS transports in E. coli E69

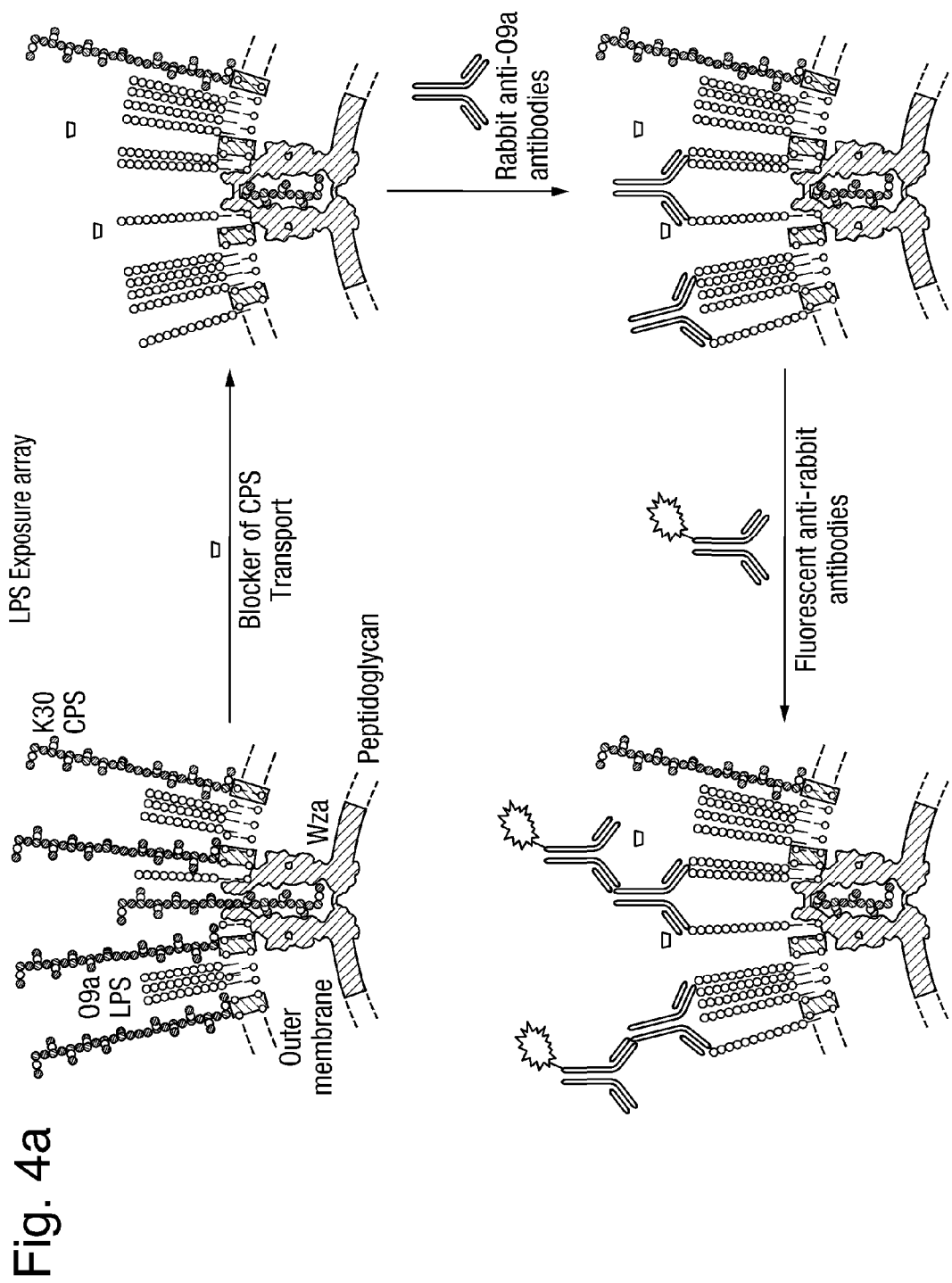

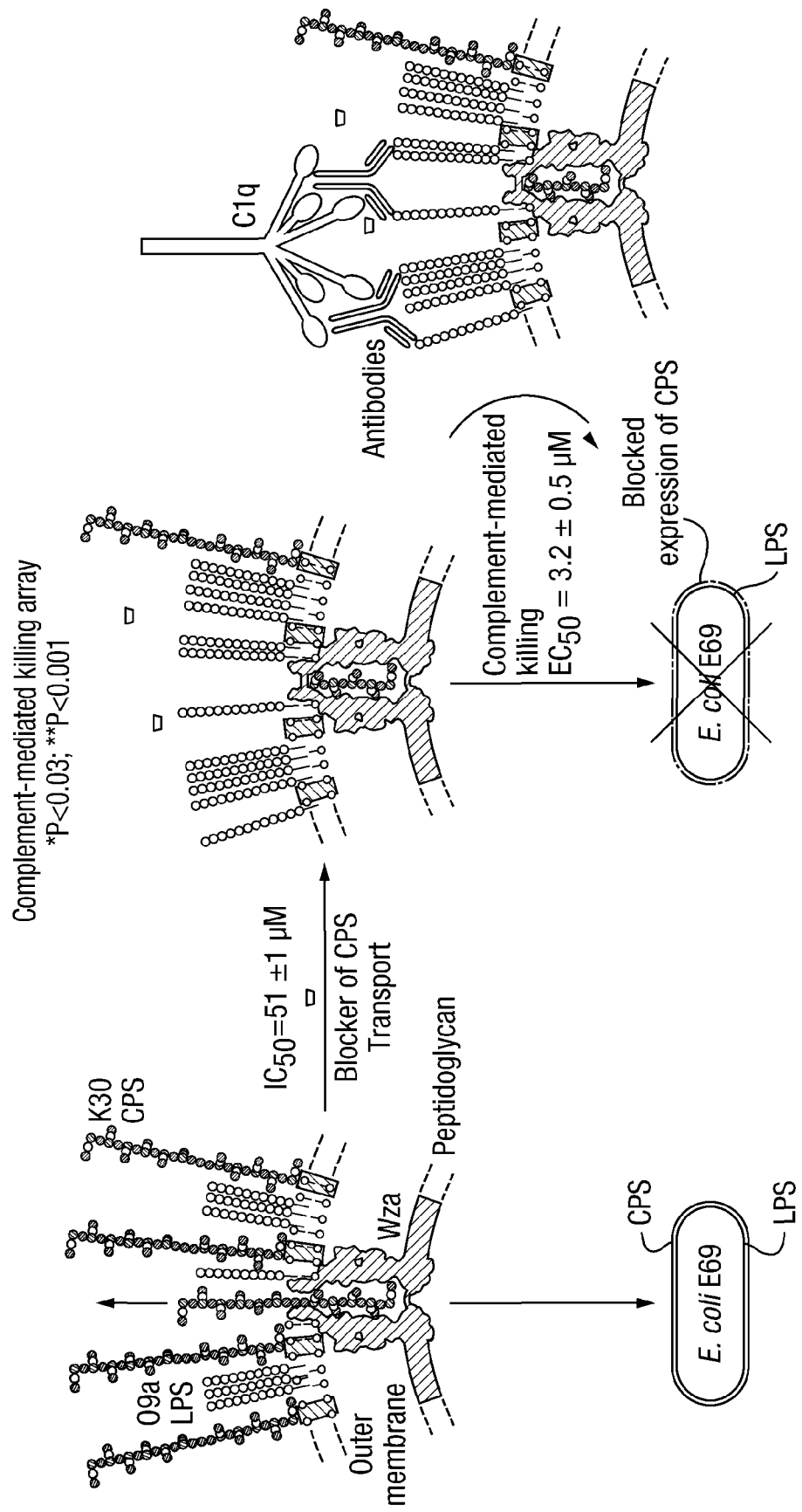

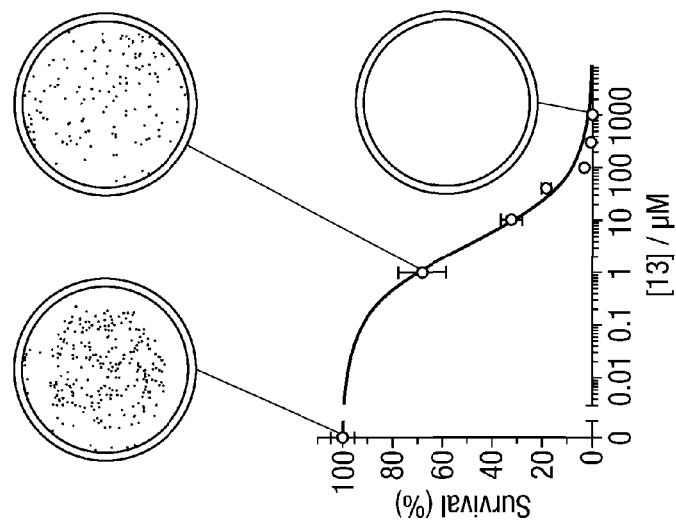
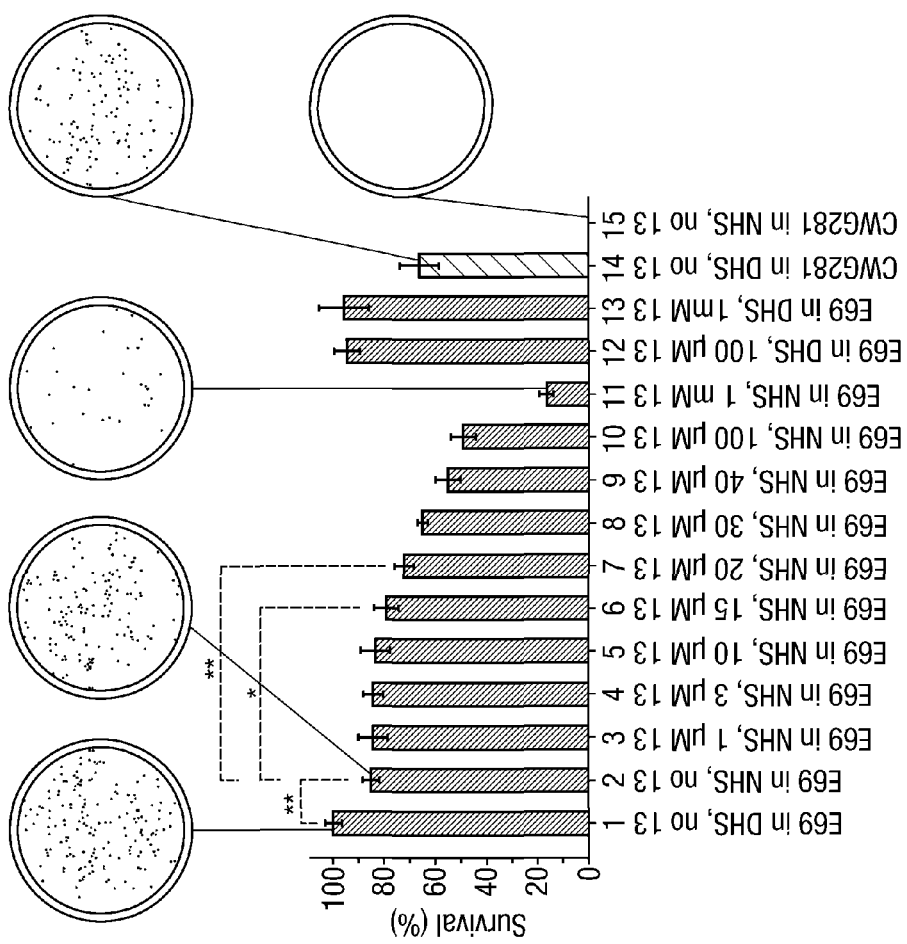

CYCLIC OLIGOSACCHARIDES FOR USE IN THE TREATMENT AND PREVENTION OF BACTERIAL INFECTION

The invention relates to compounds for use in the prevention and treatment of bacterial infection, in particular of *E. coli* infection, as well as methods for treating or preventing bacterial infection and methods for identifying compounds. The invention also relates to in vitro uses of the compounds as anti-bacterial agents, and anti-bacterial products containing the compounds.

BACKGROUND TO THE INVENTION

Modern drug discovery dates back to Alexander Fleming's confirmation of penicillin as an antibacterial agent in 1928. For the last 8 decades, many effective antibiotics have been identified and commercialized. However, bacteria have lived on the Earth for billions of years and have survived a wide range of naturally occurring antibiotics. Their resistance to antibiotics discovered by humans is therefore not surprising. In 2004, over 70% of pathogenic bacteria had generated resistance to at least one commercially available antibiotic. In addition, many evolving pathogens have caused new diseases. There is therefore a demand for new antibiotics that are active against resistant bacteria.

SUMMARY OF THE INVENTION

Capsular polysaccharides (CPS) comprise the first and most important protective layer for bacteria to protect the cell surface proteins on the outer membrane from extracellular attacks. Underneath the CPS, gram-positive bacteria have a thick peptidoglycan layer as an additional shield, while gram-negative bacteria have another lipopolysaccharide layer for further protection. The high-molecular-weight CPS surrounds the surface of bacteria and provides the bacteria with high water solubility and protection from various attacks from the immediate environment, for example immune attacks from the host. Lipopolysaccharides (LPS) lie beneath the CPS layer in greater density. There are approximately 80 different K antigens (CPS) and 170 O antigens (LPS).

The variant capsular serotypes in *E. coli*. can be divided into four groups according to serological properties, genetic and biochemical criteria. Groups 1 and 4 share the same assembly system example. Membrane protein Wza translocates K30 polysaccharide from its site of synthesis at the inner membrane of a bacterial cell to the outside of the cell where it forms the capsular polysaccharide (CPS) protective layer. Consequently, it is a key factor in the formation and maintenance of the protective capsules that surround K30-expressing strains. Several other bacteria share the Wza transporter. Examples include *Klebsiella pneumonia, Achtinobacillus suis* and *Bordetella bronchiseptica*.

The present inventors have found that blocking the channel of Wza from the extracellular side can lead to damage of the CPS layer and expose other epitopes for immune attacks. Wza has therefore been found to be a good antimicrobial target. Accordingly, the present invention provides a compound which is an inhibitor of Wza-mediated polysaccharide transport for use in a method of preventing or treating bacterial infection, which method comprises administering to a subject a single agent active in preventing or treating bacterial infection, said agent being said compound which is an inhibitor of Wza-mediated polysaccharide transport or a mixture of two or more said compounds. Also provided is a method of treating or preventing bacterial infection in a subject, which method comprises administering to said subject a single agent active in preventing or treating bacterial infection, wherein the agent is a compound which is an inhibitor of Wza-mediated polysaccharide transport or a mixture of two or more said compounds. Also provided is the use of a compound which is an inhibitor of Wza-mediated polysaccharide transport in the manufacture of a medicament for use in a method of preventing or treating bacterial infection, which method comprises administering to a subject a single agent active in preventing or treating bacterial infection, said agent being said compound which is an inhibitor of Wza-mediated polysaccharide transport or a mixture of two or more said compounds. The bacterial infection is typically one caused by *Eschericia coli, Klebsiella pneumonia, Actinobacillus suis* or *Bordetella bronchiseptica*.

A key feature of the present invention is the finding that the inhibition of Wza, and the resulting damage to the bacterial CPS layer, exposes the bacteria to attack by the subject's immune system. The CPS layer of a bacterium acts as a defence against attack by an immune system. By removing or damaging that CPS layer, antigens on the bacteria are exposed to immune attack. Accordingly the compounds of the present invention work with the subject's own immune system in a "complement killing" technique. This leads to killing of bacteria, even though the compounds of the invention are not alone able to kill bacteria.

A number of antibiotic agents which are in current therapeutic use are administered together with a potentiator in order to improve the action of the antibiotic agent. Thus, the administration of two or more agents in combination to provide the antibacterial effect is a common therapeutic technique. The present invention differs from such techniques since the compounds of the invention are not administered together with further antibacterial or antibiotic agents. Rather, the compounds of the invention are typically administered alone, and are the sole active agent for use in preventing or treating the bacterial infection which is administered to the subject. Thus, the compounds of the invention do not act as potentiators for further antibiotic or antibacterial agents, but rather act as effective potentiators for the subject's own immune system.

The present inventors have found a series of compounds which inhibit Wza-mediated polysaccharide transport and accordingly the present invention also provides a compound which is a cyclic oligosaccharide of formula (I) or a pharmaceutically acceptable salt thereof, for use in a method of preventing or treating bacterial infection, which method comprises administering to a subject a single agent active in preventing or treating bacterial infection, said agent being said compound which is a cyclic oligosaccharide of formula (I) or pharmaceutically acceptable salt thereof, or a mixture of two or more said compounds;

wherein n is 0, 1, 2, 3 or 4; and
each S is the same or different and represents a saccharide unit, wherein one or more S units is modified at the primary carbon position by replacement of the hydroxyl group with a functional group X which is positively charged, or which bears a positive charge when in aqueous solution at pH 7, each group X being the same or different.

Also provided is a method of treating or preventing bacterial infection in a subject, which method comprises administering to said subject a single agent active in preventing or treating bacterial infection, wherein said agent is a compound as defined above, or a mixture of two or more said compounds. Also provided is the use of a compound as defined above in the manufacture of a medicament for use in a method of preventing or treating bacterial infection, which method comprises administering to a subject a single agent active in preventing or treating bacterial infection, said agent being a compound as defined above, or a mixture of two or more said compounds.

The present invention also provides a compound which is a cyclic oligosaccharide of formula (I) or a pharmaceutically acceptable salt thereof:

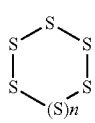

(I)

wherein n and S are as defined above, other than cyclodextrins wherein each saccharide unit S is modified at the C6 position. Also provided is a pharmaceutical composition comprising the compound and a pharmaceutically acceptable carrier or diluent.

Anti-bacterial agents are useful not only in therapeutic treatments of bacterial infections, but also in vitro, in particular to kill bacteria outside the body, or to inhibit growth or replication of bacteria outside the body. The compounds described herein are therefore also useful as in vitro anti-bacterial agents. For instance, the compounds described herein may be used in a method, typically an in vitro method, of killing bacteria or of inhibiting the growth or replication of bacteria in a substance or on a surface, which method comprises treating said substance or surface with a compound as described herein. For in vitro use, the compounds administered typically have an 8-membered saccharide ring, thus in formula (I), n=3. Further, for in vitro use, the immune-mediated killing technique described above will not be effective. Thus, the compounds are typically used in combination with antibacterial agents when used in vitro.

The invention also provides a product comprising a compound as described herein, wherein said product is a cleaning agent, a fabric or a polymeric material.

BRIEF DESCRIPTION OF THE FIGURES

FIG. 1 depicts the results of a channel recording with wt Wza;

FIG. 2 provides the results of a staining assay to determine the inhibitory effects of a number of different cyclodextrins in differing concentrations.

FIG. 4 shows the effects of inhibitors of CPS transport on O9a LPS exposure to O9a-specific LPS antibodies in E69.

FIG. 4a shows the design of an experiment to measure the exposure of O9a LPS in *E. coli* strains E69 and CWG281.

FIG. 5 shows the effects of $am_8\gamma CD$ 13 on complement-mediated killing of E69. FIG. 5a shows the mode of action of $am_8\gamma CD$ 13. FIG. 5b shows survival of strains E69 (Bars 1-13) and CWG281 (Bars 14-15) in the presence of normal human serum (NHS) or deactivated human serum (DHS). Representative LB-Agar plates corresponding to bars 1, 2, 11, 14 and 15 are shown. FIG. 5c shows the effects of various concentrations of am8γCD on complement-mediated killing of *E. coli* E69. Representative LB-Agar plates corresponding to no treatment with $am_8\gamma CD$ 13, treatment with 1 µM, 1 mM of $am_8\gamma CD$ 13 are shown.

DETAILED DESCRIPTION OF THE INVENTION

Inhibitor Compounds

Figure 3A:
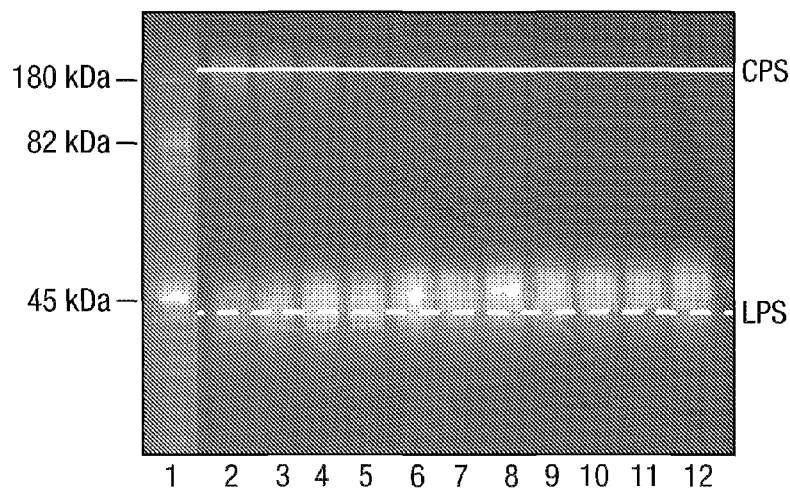
FIG. 3a provides the results of a staining assay using different concentrations of $am_8\gamma CD$.

A compound which is an inhibitor of Wza-mediated polysaccharide transport as used herein is a compound which interferes with or blocks polysaccharide transport by Wza, typically by interfering with or blocking passage of polysaccharides through the Wza channel. To determine whether a compound is an inhibitor of Wza-mediated polysaccharide transport, a compound can be subjected to the screening method described herein. In particular, the compound can be tested by using a staining method in accordance with Example 4 described herein. A compound is considered an inhibitor of Wza-mediated polysaccharide transport herein if polysaccharide transport in the staining assay is inhibited in comparison with a control containing no inhibitor compound. Preferably, an inhibitor of Wza-mediated polysaccharide transport provides a 50% fluorescent intensity of CPS compared to a control, typically with a concentration of the compound of no more than 5 mM, preferably no more than 2 mM or 1 mM.

Typically, the compounds are inhibitors of Wza-mediated K30 polysaccharide transport. Particular examples of compounds which have been identified by the inventors to inhibit Wza-mediated polysaccharide transport are cyclic oligosaccharides, for example cyclodextrins. These cyclic oligosaccharides are typically modified so that they include at least one functional group which is positively charged under physiological conditions. Typically, each saccharide unit of the cyclic oligosaccharide carries such a functional group. The positively charged functional groups facilitate binding of the compound across the extracellular side of the Wza channel, thus blocking the channel. The Wza channel itself is octameric, and thus to provide maximum binding efficiency, the cyclic oligosaccharide preferably comprises a ring of 8 saccharide units.

The invention particular relates to compounds having the formula (I):

(I)

wherein n and S are as defined above. In formula (I), n is preferably 1, 2 or 3, in particular 3. Where n is 3, the oligosaccharide has 8 saccharide units which, as described above, maximises binding across the Wza channel.

The saccharide units S may be the same or different, but typically are the same. The saccharide may be a pentose saccharide or a hexose saccharide and is typically a hexose saccharide. Examples of suitable saccharide units are glucose, galactose or mannose or a derivative thereof. In one embodiment each saccharide unit is the same or different and represents glucose or a derivative thereof. The saccharide units may be in either D or L form, or a combination of D and L form saccharide units may be present. Typically, either all saccharide units have D form or all saccharide units have L form.

When S represents a hexose saccharide unit, typically the functional group X is present at the primary C6 position. When S represents a pentose saccharide unit, typically the functional group X is present at the primary C5 position.

The saccharide units are typically linked via the C1 and C4 positions of the saccharide, i.e. each bond is a C1→C4 bond. Alternative configurations are also possible.

Each saccharide unit may be unmodified, or modified, but at least one saccharide unit is modified at the primary carbon position (the C6 position in the case of a hexose saccharide) by replacement of the OH group with a functional group X which bears a positive charge under physiological conditions, i.e. in aqueous solution at pH 7. Where more than one group X is present, each group X may be the same or different. Typically, at least 6 saccharide units are modified to carry a group X at the primary carbon atom (in which case n is 1, 2, 3 or 4), for example at least 7 saccharide units may be modified to carry a group X at the primary carbon atom (in which case n is 2, 3 or 4), or at least 8 saccharide units may be modified to carry a group X at the primary carbon atom (in which case n is 3 or 4).

As used herein, a group X is a group which bears a positive charge under physiological conditions, i.e. in aqueous solution at pH 7, and includes cations, for example X may comprise a group —$NH_3^+$ or a derivative thereof. The group X may alternatively be uncharged, but become protonated under physiological conditions, for example X may comprise a —$NH_2$ group or a derivative thereof. Therefore, X includes groups which are positively charged (cations) as well as groups which comprise a base which will be protonated when in aqueous solution. The skilled person is well aware of suitable functional groups or could test whether a chosen group is basic in aqueous solution by determining whether it has a pH of greater than 7.0 when dissolved in water. For example, X may comprise an amine group or a guanidine group or a derivative thereof. The cyclic oligosaccharide may be provided as a salt, in which case the group X is protonated to form a protonated amine or guanidine group or a derivative thereof, for example an —$NH_3^+$ group.

Preferably, X comprises an amine group, either in its free base or salt form. The amine group may be primary, secondary or tertiary. A tertiary amine will typically be present in salt form. Primary amines are preferred. Typically X comprises an —$NH_3^+$ group.

In one embodiment of the invention, each X is the same or different and represents a group of formula (II):

$$-(Alk_1)_p\text{-}(Ar)_q\text{-}(Alk_2)_r\text{-}A \quad (II)$$

wherein:
p, q and r independently represent 0 or 1;
$Alk_1$ represents a straight or branched $C_{1-6}$ alkylene group wherein one or more of the $CH_2$ groups is optionally replaced with a heterogroup selected from —O—, —S—, —NR—, —NRCO—, —NRCO—, —CONR, —CO—, —OCO— and —COO—, and wherein one or more of the $CH_2$ groups is optionally substituted with a substituent selected from OR, SR, NRR', $CH_2OR$, $CH_2SR$ and $CH_2NRR'$, wherein R and R' independently represent H or a $C_{1-2}$ alkyl group; Ar represents phenyl;

$Alk_2$ represents methylene or ethylene; and

A represents —$NR_2$ or

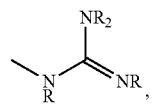

wherein each R is the same or different and represents H or a $C_{1-2}$ alkyl group, and wherein A may be in the form of a free base or may be protonated to form a cation.

Typically, either p=q=r=1; or q=r=0 and s=0 or 1.

$Alk_1$ is typically a straight or branched $C_{1-6}$ alkylene group, for example a straight or branched $C_{1-4}$ alkylene group, for example a $C_{1-2}$ alkylene group. For example, $Alk_1$ may be a straight chain alkylene group such as methylene, ethylene, n-propylene or n-butylene. One or more, typically one, of the $CH_2$ groups is optionally replaced with a heterogroup selected from —O—, —S—, —NR—, —NRCO—, —CONR, —CO—, —OCO— and —COO—. Typically, either no heterogroup is present, or one heterogroup is present selected from —O—, —S—, —NR—, —NRCO— and —CONR. R is H or a $C_{1-2}$ alkyl group, preferably H.

$Alk_1$ is unsubstituted or substituted. Where $Alk_1$ is substituted, one or more, preferably one, of the $CH_2$ groups is substituted. In one embodiment the substituents are selected from OR, SR and NRR', for example NRR' wherein R and R' independently represent H or a $C_{1-2}$ alkyl group, for example —$NH_2$.

Ar is a phenyl group which is unsubstituted or substituted. Examples of suitable substituents are $C_{1-2}$ alkyl groups, OR, SR, NRR', $CH_2OR$, $CH_2SR$ and $CH_2NRR'$, wherein R and R' independently represent H or a $C_{1-2}$ alkyl group. Particular examples are NRR', wherein R and R' independently represent H or a $C_{1-2}$ alkyl group, for example —$NH_2$. Typically, Ar is unsubstituted or carries one or two substituents. For example, Ar is unsubstituted.

$Alk_2$ is unsubstituted or substituted. Examples of suitable substituents are OR, SR, NRR', $CH_2OR$, $CH_2SR$ and $CH_2NRR'$, wherein R and R' independently represent H or a $C_{1-2}$ alkyl group. Particular examples are NRR', wherein R and R' independently represent H or a $C_{1-2}$ alkyl group, for example —$NH_2$. Typically, $Alk_2$ is unsubstituted or carries one substituent. For example, $Alk_2$ is unsubstituted.

A is typically —$NH_2$ or

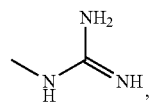

in either free base or protonated form.

In one embodiment, the groups X are the same or different and are selected from

 (IIA)

wherein p is 0 or 1;

$Alk_1$ represents a straight or branched $C_{1-4}$ alkylene group wherein one of the $CH_2$ groups is optionally replaced with a heterogroup selected from —O—, —S—, —NR—, —NRCO— and —CONR, and wherein one or more of the $CH_2$ groups is optionally substituted with a substituent selected from OR, SR, NRR', wherein R and R' independently represent H or a $C_{1-2}$ alkyl group; and A is —$NH_2$ or

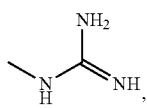

in the free base or cationic form.

Examples of suitable functional groups X are —($C_{0-4}$alkyl)-A, —O—($C_{1-3}$alkyl)-A, —S—($C_{1-3}$alkyl)-A and —NHCO—($C_{1-2}$alkyl)-A, wherein A is —$NH_2$ or

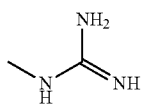

in either the free base or cationic form and wherein the alkylene groups are unsubstituted or substituted with —$(CH_2)_{0-1}$—$NH_2$, —$(CH_2)_{0-1}$—OH, —$(CH_2)_{0-4}$—SH.

Further examples of functional groups X are

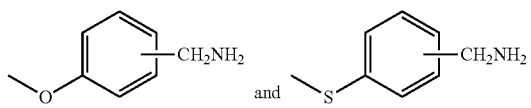

in either free base or cationic form

In one embodiment the functional group X is —$NH_2$ or —$NH_3^+$.

One or more of the saccharide units S may be modified at positions other than the primary carbon atom position. In the case of a hexose saccharide, such modifications are typically located at either the C2 or C3 position, or both, since the cyclic structure is typically formed by C1→C4 linkages. The modifications are not particularly limited and include, for example, replacement of the OH group with hydrogen or with a group such as a functional group Y or $C_{1-6}$ alkyl which is unsubstituted or substituted with a functional group Y, wherein Y is selected from OR, SR, NRR', carboxylate, phosphate or sulphonate, wherein R and R' are independently H or $C_{1-2}$ alkyl.

Examples of cyclic oligosaccharides of formula (I) are the cyclodextrins of formulae (IA), (IB) or (IC):

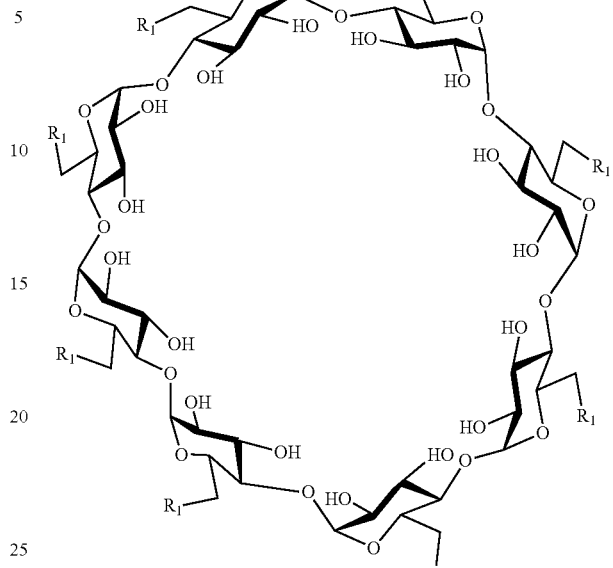
(IA)

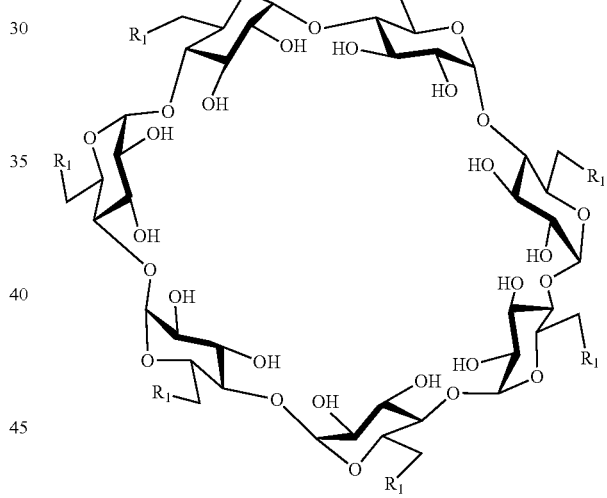
(IB)

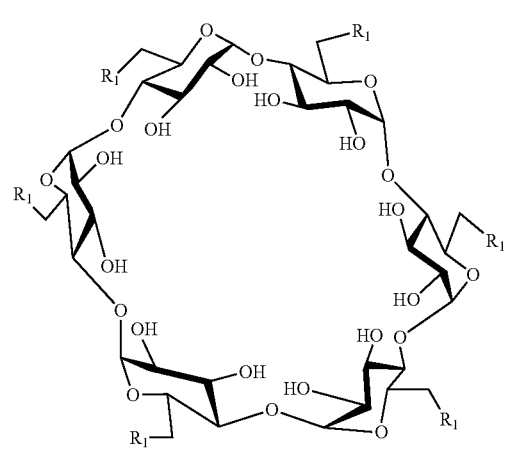
(IC)

wherein each $R_1$ is the same or different and is selected from OH or a group X as defined herein. Typically X is —$NH_2$ or $NH_3^+$. At least 6, for example at least 7 or 8 of the groups $R_1$ represent a group X. Preferred cyclic oligosaccharides are those of formula (IA) above.

The OH groups at positions C2 and C3 in formulae (IA), (IB), and (IC) may be modified as described herein.

Compounds containing one or more chiral centre may be used in enantiomerically or diastereoisomerically pure form, or in the form of a mixture of isomers. For the avoidance of doubt, the compounds described herein can, if desired, be used in the form of solvates. Further, for the avoidance of doubt, the compounds described herein may be used in any tautomeric form.

As used herein, a salt of a compound is typically a pharmaceutically acceptable salt. A salt is typically a salt with an acid, for example a pharmaceutically acceptable acid. Pharmaceutically acceptable acids include both inorganic acids such as hydrochloric, sulphuric, phosphoric, diphosphoric, hydrobromic or nitric acid and organic acids such as citric, fumaric, maleic, malic, ascorbic, succinic, tartaric, benzoic, acetic, methanesulphonic, ethanesulphonic, benzenesulphonic or p-toluenesulphonic acid.

The present invention also provides prodrugs of the compounds described herein. A prodrug is an analogue of a compound which will be converted in vivo to the desired active compound. Examples of suitable prodrugs include compounds of formula (I) in which a nitrogen atom is quaternised by addition of an ester or alkyl ester group. For example, the nitrogen atom of an amine group at position A may be quaternised by addition of a —$CH_2$—O—COR group, wherein R is typically methyl or tert-butyl. Other suitable methods will be known to those skilled in the art. Further suitable prodrugs include compounds which have been modified at a carboxylic acid group to form an ester, or at hydroxyl group to form an ester or carbamate.

Synthesis

The compounds described herein can in some instances be obtained from commercial sources, or novel compounds may be prepared using techniques familiar to the skilled chemist. Information on the synthesis of cyclic oligosaccharides can be found in Gattuso et al, Chem. Rev. 1998, 98, 1919-1958; Wenz et al, Chem. Rev. 2006, 106, 782-817 and Engeldinger et al, Chem. Rev. 2003 Vol 103, No. 11, 4147-4173.

By way of example, cyclodextrins having 5 to 8 saccharide units can be prepared in accordance with the techniques described by Gattuso et al, Chem. Rev. 1998, 98, 1919-1958, in particular pages 1926 onwards. The skilled person would be able to adapt these techniques to provide alternative cyclic oligosaccharides by varying the starting saccharide unit.

Modifications on the cyclic saccharide unit can be made either before or after formation of the cyclic structure. Typically, the basic saccharide unit will be modified before formation of the cyclic structure as this gives greater latitude with regard to which positions of the saccharide unit are modified. Modification can be carried out be routine selection and deprotection techniques. Exemplary syntheses of modified cyclic oligosaccharides are provided by Gattuso et al, Chem. Rev. 1998, 98, 1919-1958, in particular pages 1931 onwards.

An exemplary scheme for the synthesis of 6 or 8 membered cyclic oligosaccharides linked via C1-C4 is as follows:

Scheme 1

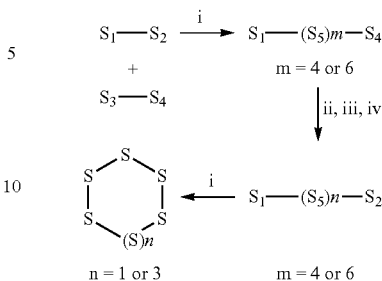

In scheme 1, S1 to S5 are identical to the groups S as defined herein with the following changes:
S1 has an OAc group at the C4 position, which is to be linked to the next sugar in the cyclic structure;
S2 is a reactive sugar having a F group at the C1 position;
S3 has an OH at the C4 position; and
S4 has an OA11 group at the C1 position.

Other positions of the saccharide units S1 to S5 may bear modifications, for example at position C6. Where a reactive group or an OH group is present at the C2, C3, C5 or C6 positions, protective groups (e.g. Bn for protecting an OH group) are typically used to protect these positions.

In step (i), the two disaccharides are linked by reaction with $SnCl_2$/AgOTf. The reaction may be stopped after either one or two additions of disaccharide in order to provide either a 6 or an 8 saccharide unit chain. The end groups on the chain are then altered by reaction with (ii) ($ClCH_2CO)_2O$/DCE/$C_2H_5N$; (iii) $PdCl_2$/AcOH; and then (iv) $SO_2Cl_2$/DMF. The acetyl group on sugar S1 is then removed by reaction in NaOMe/MeOH/THF and then the chain is cyclised by reaction with $SnCl_2$/AgOTf. Protecting groups are then removed to provide the compounds described herein, for example Bn groups are removed by reaction in $H_2$/Pd/C/THF-MeOH/$H_2O$.

An alternative synthesis, which leads to 6, 7 or 8-membered cyclic oligosaccharide chains is as follows:

Scheme 2

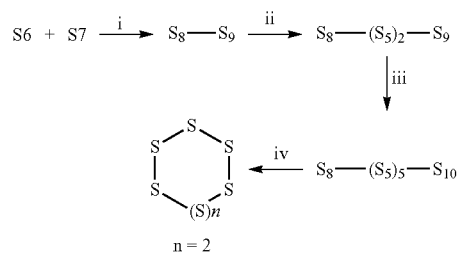

In Scheme 2, S5 to S10 are identical to the groups S as defined herein with the following changes:
S6 has a $ClCH_2COO$ group at the C4 position, and a O—(C=NH)—$CCl_3$ group at the C1 position;
S7 has a p-$MeOC_6H_4O$ group at the C1 position and an OH group at the C4 position;
S8 has a $ClCH_2COO$ group at the C4 position;
S9 has a p-$MeOC_6H_4O$ group at the C1 position; and
S10 has an SMe group at the C1 position.

Other positions of the saccharide units S5 to S10 may bear modifications, for example at position C6. Where a reactive group or an OH group is present at the C2, C3, C5 or C6 positions, protective groups (e.g. Bn for protecting an OH group) are typically used to protect these positions.

In a first stage, sugars S6 and S7 are coupled in the presence of TMSOTf/mol sieves 4 A/DCE to provide disaccharide S8-S9. The ClCH$_2$COO temporary protecting group at the C4 position of S8 can then be removed by reaction in (NH$_4$)$_2$Ce(NO$_3$)$_6$/MeCN/H$_2$); CCl$_3$CN/DBU/DCE and the resulting compound coupled with a further S6 molecule. These steps can be repeated to provide the desired chain length. In the depicted figure in Scheme 2, the reaction conditions for step (iii) are: (a) (NH$_4$)$_2$Ce(NO$_3$)$_6$/MeCN/H$_2$); (b) CCl$_3$CN/DBU/DCE; (c) Bu$_3$SnSMe/BF$_3$OEt$_2$/DCE; (d) (NH$_4$)$_2$CS/EtOH; (e) coupling with trisaccharide S8-S5-S11, wherein S11 is a saccharide unit S having a O—(C=NH)—CCl$_3$ group at the C1 position, with C2, C3, C5 and C6 either modified or protected. Coupling takes place in the presence of TMSOTf/mol sieves 4 Å/DCE. The resulting heptasaccharide is then subjected to protecting group interconversion and cyclised in step (iv): (a) (NH$_4$)$_2$CS/EtOH; (b) EtOCH=CH$_2$/PPTS/DCE; (c) NaOMe/MeOH; (d) BnBr/NaH/DMF; (e) Amberlyst 15 resin/CHCl$_3$/MeOH; (f) PhSeOTf/DCE, —20° C.; (g) H$_2$/Pd/C/MeOH.

To produce a cyclic oligosaccharide which is linked other than via the C1, C4-positions, the above syntheses can be adapted to provide the reactive groups at the desired positions. For example, to produce a cyclic oligosaccharide which is linked via the C1-C3 positions, S1 and S3 in Scheme 1 above would be modified so that the OAc and OH groups respectively are at the C3 position.

As starting materials for Schemes 1 and 2, the sugars S1-S2, S3-S4, S6 and S7 are typically commercially available, or can be produced using standard techniques. For example, the skilled person could modify a saccharide unit at the C6 position to bear a functional group by reaction of the C6OH group with PPh$_3$ and iodine in DMF at 70° C., followed by (i) reaction with NaN$_3$, DMF, 60° C.; and (ii) reaction with PPh$_3$ in DMF at room temperature and subsequently NH$_4$OH for 24 hrs at room temperature. The modification can be carried out either on the single saccharide unit prior to formation of a cyclic oligosaccharide, or alternatively all C6 positions of a cyclic oligosaccharide can be modified together as follows in Scheme 3:

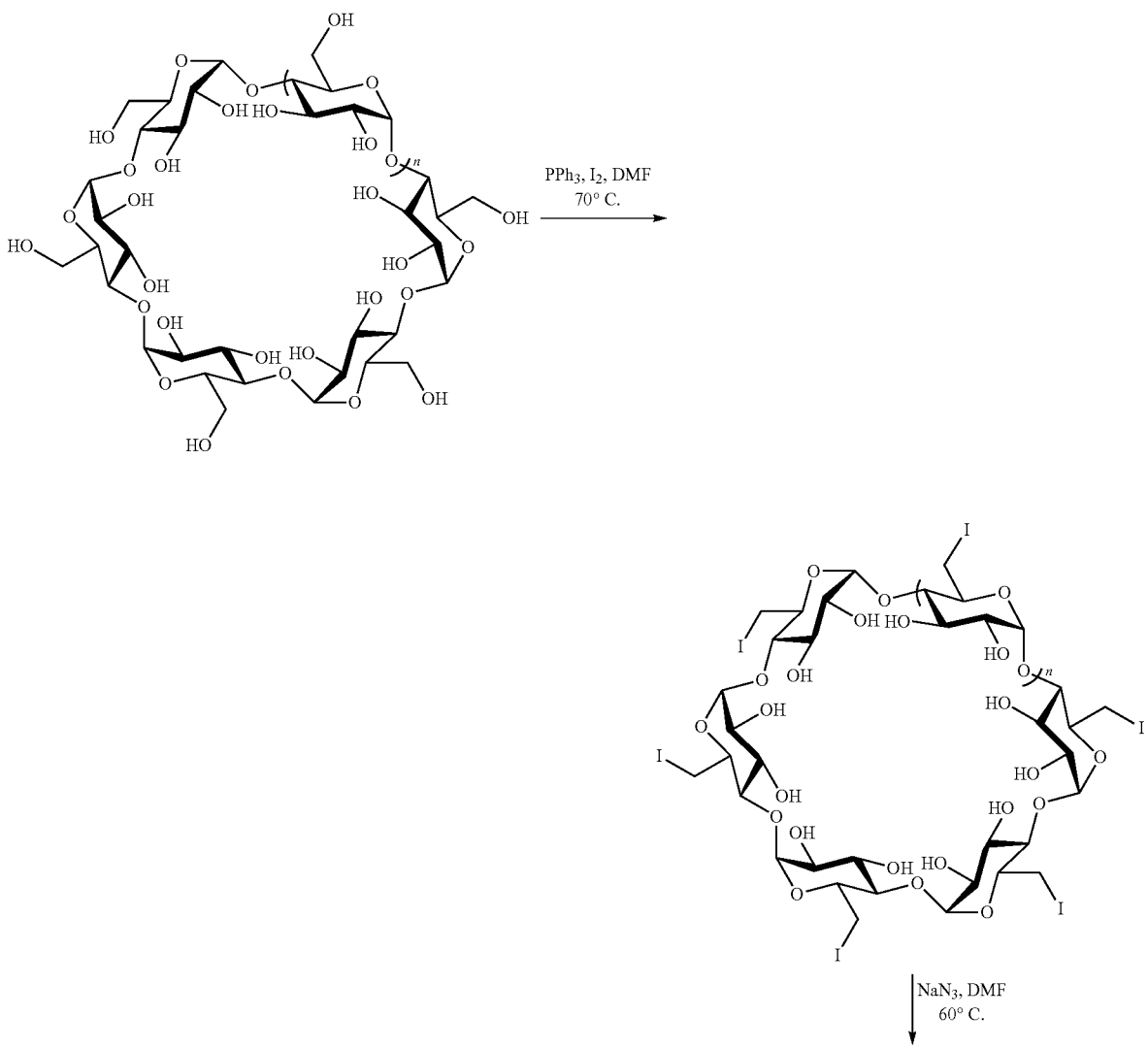

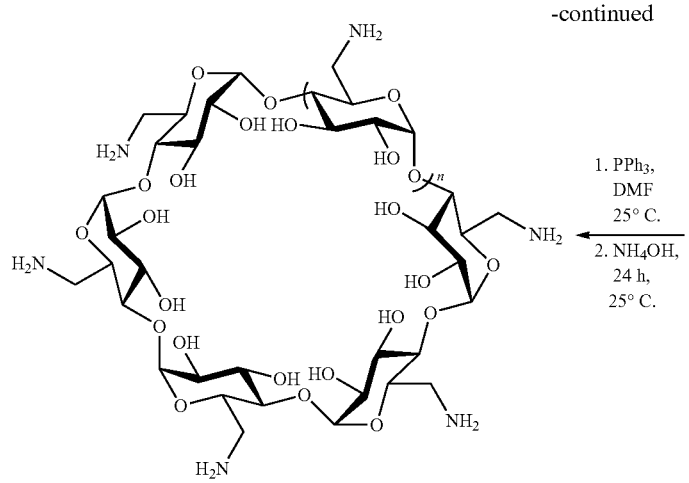

(Ref: *J. Org. Chem.* 1996, 61, 903-908)

-continued

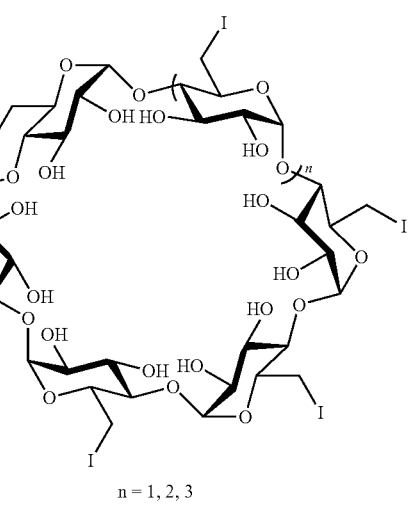

n = 1, 2, 3

The above syntheses provide methods for the preparation of hexose saccharide-containing structures. The skilled person would be familiar with corresponding techniques to produce pentose saccharides.

Medical Treatments

The compounds described herein inhibit the action of Wza by binding to the extracellular opening of the Wza channel and thereby inhibiting the transport of polysaccharides by Wza from within the cell to the CPS layer. In particular, the compounds have been found to inhibit K30 polysaccharide transport. The compounds thereby prevent or inhibit the formation of the CPS layer of the bacterium, leaving the cell open to attack by the immune system. Thus, the compounds are effective in killing or preventing or inhibiting the growth or replication of bacteria in immune environments.

The compounds of the invention can therefore be used in a method of removing or reducing the thickness of the CPS layer of a bacterium, which method comprises exposing the bacterium to a compound of the invention. Such methods can be carried out either in vivo or in vitro. A compound of the invention may thus be for in vivo use in a method of removing or reducing the thickness of the CPS layer of a bacterium. Further, the compounds of the invention may be used in the manufacture of a medicament for removing or reducing the thickness of the CPS layer of a bacterium in vivo.

The removal or reduction in thickness of the CPS layer can be determined via the change in cell wall thickness (typically reduced to no more than 50 nm) or by studying the degree of exposure of underlying layers caused by treatment with a compound of the invention, for example, by carrying out the method of Example 5 and studying the increase in exposure of the LPS layer caused by the compounds of the invention. Typically, the exposure of the underlying layers is at least 10% compared to a control lacking a CPS layer, preferably at least 20%, more preferably at least 50%.

In accordance with the present invention, the compounds described herein are administered as the sole agent active in preventing or treating bacterial infection in vivo. Thus, the compounds described herein are the sole agent having in vivo bactericidal effect which is administered to the subject. An agent having in vivo bactericidal effect as used herein is an agent which when used alone causes killing of bacteria in an in vivo environment. This term accordingly includes antibacterial agents which themselves kill bacteria, as well as compounds such as those of the invention which have bactericidal effect through immune complement-killing. The concept of in vivo bactericidal effect is well known and standard tests such as the serum bactericidal test (Clinical Microbiology Reviews, January 1988, 19-26) or the procedure set out in Example 6 can be used to determine whether any compound has an in vivo bactericidal effect. Typical compounds having in vivo bactericidal properties will shows a level of bacterial killing of at least 10% above control levels following incubation of the compound at a concentration of 1 mM in serum for 10 hours at 37° C. (e.g. by following the procedure of Example 6 herein).

The compounds of the present invention are administered in the absence of antibacterial agents. The concept of antibacterial agents is very well known in the art and includes any compound capable of killing bacteria alone, both in vivo and in vitro. The term antibacterial agent accordingly does not include compounds of the invention which do not kill bacteria alone when used in vitro. Typically, the active ingredient which is administered consists of a single agent active in preventing or treating bacterial infection (i.e. a single agent having in vivo bactericidal effect), said agent consisting of a compound of the invention or a mixture of two or more compounds of the invention. Typically, no further active ingredients are administered in the same treatment. Administration is thus typically of a single active ingredient consisting of a compound of the invention, preferably a cyclic oligosaccharide of formula (I) or a pharmaceutically acceptable salt thereof.

In one aspect, the invention comprises administering a pharmaceutical composition to the subject, the composition consisting of one or more compounds of the invention and one or more pharmaceutically acceptable carriers and/or diluents. Preferably, the composition which is administered consists of a cyclic oligosaccharide of formula (I) or a pharmaceutically acceptable salt thereof and one or more pharmaceutically acceptable carriers and/or diluents. Typically, the method of administration consists of administering one pharmaceutical composition to the subject, the composition being as defined above.

The compounds described herein may therefore be used to treat or prevent bacterial infection, typically infection caused by a bacterium containing the Wza protein. Bacteria containing Wza protein are described in Microbiology and Molecular Biology Reviews, 73: 155-177, and the bacterial infections which can be prevented or treated in accordance with the present invention are, for example, bacterial infections caused by the bacteria mentioned in this review. Particular examples of such bacteria are *Acinetobacter Venetianus, Eschericia coli, Klebsiella pneumonia, Achtinobacillus suis* or *Bordetella bronchiseptica*, for example *Acinetobacter Venetianus* (RAG-1); *Escherichia coli* (colanic acid), *Escherichia coli* (K30), *Klebsiella Pneumonia* (KJ); *Actinobacillus* suis (SO4-K1); *Bordetella Bronchiseptica* (RB50); in particular *Eschericia coli, Klebsiella pneumonia, Achtinobacillus suis* or *Bordetella bronchiseptica*, most particularly *Eschericia coli* (e.g. colonic acid or K30).

The bacterial infections which are treated or prevented in accordance with the invention may also be caused by bacteria containing homologs of Wza, for example bacteria containing a protein having at least 60%, preferably at least 75%, 80%, 85% or 90% identity with Wza; or bacteria contain a protein having at least 95%, 98% or 99% identity with Wza. EMBO Journal Vol. 19 No. 1 pp. 57-66, 2000 describes such homologs and the bacteria containing them and the present invention accordingly in one embodiment relates to the treatment or prevention of bacterial infections caused by the bacteria mentioned in this Journal.

The compounds described herein may be used in the treatment or prevention of diseases caused by bacterial infection, in particular gastroenteristis, urinary tract infections and pneumonia.

In one embodiment, the compounds described herein are used to treat of prevent infections caused by bacteria other than *Staphylococcus aureus*.

The compounds described herein may be administered in a variety of dosage forms. Thus, they can be administered orally, for example as tablets, troches, lozenges, aqueous or oily suspensions, dispersible powders or granules. The compounds as described herein may also be administered parenterally, either subcutaneously, intravenously, intramuscularly, intrasternally, transdermally or by infusion techniques. The compounds may also be administered as suppositories. The compounds may be administered by inhalation in the form of an aerosol via an inhaler or nebuliser.

A compound as described herein is typically formulated for administration with a pharmaceutically acceptable carrier or diluent in the form of a pharmaceutical composition. Preferred pharmaceutical compositions are sterile and pyrogen free. For example, solid oral forms may contain, together with the active compound, solubilising agents; diluents, e.g. lactose, dextrose, saccharose, cellulose, corn starch or potato starch; lubricants, e.g. silica, talc, stearic acid, magnesium or calcium stearate, and/or polyethylene glycols; binding agents; e.g. starches, arabic gums, gelatin, methylcellulose, carboxymethylcellulose or polyvinyl pyrrolidone; disaggregating agents, e.g. starch, alginic acid, alginates or sodium starch glycolate; effervescing mixtures; dyestuffs; sweeteners; wetting agents, such as lecithin, polysorbates, laurylsulphates; and, in general, non-toxic and pharmacologically inactive substances used in pharmaceutical formulations. Such pharmaceutical preparations may be manufactured in known manner, for example, by means of mixing, granulating, tabletting, sugar-coating, or film coating processes.

Liquid dispersions for oral administration may be solutions, syrups, emulsions and suspensions. The solutions may contain solubilising agents. The syrups may contain as carriers, for example, saccharose or saccharose with glycerine and/or mannitol and/or sorbitol.

Suspensions and emulsions may contain as carrier, for example a natural gum, agar, sodium alginate, pectin, methylcellulose, carboxymethylcellulose, or polyvinyl alcohol. The suspensions or solutions for intramuscular injections may contain, together with the active compound, a pharmaceutically acceptable carrier, e.g. sterile water, olive oil, ethyl oleate, glycols, e.g. propylene glycol; solubilising agents, e.g. lidocaine hydrochloride. Solutions for intravenous or infusions may contain as carrier, for example, sterile water and solubilising agents, preferably they may be in the form of sterile, aqueous, isotonic saline solutions.

A therapeutically effective amount of a compound described herein is administered to a patient. A typical daily dose is up to 50 mg per kg of body weight, for example from 0.001 to 50 mg per kg of body weight, according to the activity of the specific compound, the age, weight and conditions of the subject to be treated, the type and severity of the disease and the frequency and route of administration. Preferably, daily dosage levels are from 0.05 mg to 2 g, preferably from 0.1 mg to 10 mg, e.g. up to 5 mg or 1 mg. The compound of the invention is typically administered to the patient in a non-toxic amount.

Other Uses

The compounds of the invention are active as antibacterial agents not only as therapeutic agents, but also for use in vitro. For example, the compounds may be incorporated into cleaning agents such as soaps, detergents and deodorizers. Alternatively, the compounds may be incorporated into fabrics to provide anti-bacterial fabrics for use in, for example, clothing such as sportswear, furniture coverings such as seat coverings and fabrics used in the medical field such as dressings or plasters.

The compounds may also be incorporated into polymeric materials such as plastics. These materials can be used in articles for food preparation and storage such as chopping boards and food storage containers as well as devices used in a medical context, for example door handles and other surfaces in hospitals, and medical devices or packaging for medical devices.

The compounds of the invention can advantageously be used in combination with other anti-bacterial or anti-microbial agents. In this way, the exposure of the bacterium via the weakening of the CPS layer of the cell can be used to improve the performance of other antibacterial agents. In one embodiment, the compounds of the invention are used in combination with antimicrobial peptides, for example those mentioned in Microbiology (2008), 154, 3877-3886.

Drug Screening

The present invention also describes methods for screening compounds for their ability to prevent or treat a bacterial infection. Compounds screened as described herein are preferably able to inhibit Wza-mediated polysaccharide transport in the bacteria causing the infection. Compounds that inhibit Wza-mediated polysaccharide transport in the bacteria are suitable for treating or preventing an infection by the bacteria. The drug screening methods described herein allow large numbers of compounds to be screened quickly. Suitable bacteria are discussed above.

Any compound may be used. Suitable compounds include, but are not limited to, proteins, polynucleotides, small molecules, natural products and carbohydrates. The carbohydrate is preferably a cyclic oligosaccharide, such as a cyclodextrin.

The screening methods described herein may be carried out in any way. A preferred embodiment of the screening method is disclosed in the Examples.

The screening method described herein may comprise (a) measuring Wza-mediated polysaccharide transport in a sample of the bacteria in the absence of the compound, (b) contacting the sample with the compound; and (c) measuring the Wza-mediated polysaccharide transport in the sample in the presence of the compound and thereby determining whether or not the compound inhibits Wza-mediated polysaccharide transport in the bacteria. A decreased transport in the presence of the compound compared with the absence of the compound identifies the compound as being able to inhibit Wza-mediated polysaccharide transport in the bacteria. An increase or no change in the transport in the presence of the compound compared with the absence of the compound identifies the compound as not being able to inhibit Wza-mediated polysaccharide transport in the bacteria.

The screening method may comprise (a) providing a test sample of the bacteria, (b) contacting the test sample with the compound; (c) measuring Wza-mediated polysaccharide transport in the test sample of the bacteria in the presence of the compound; and (d) comparing the transport measured in the test sample with a control value obtained using a control sample of the bacteria which has not been contacted with the compound and thereby determining whether or not the compound inhibits Wza-mediated polysaccharide transport in the bacteria. A decreased transport in the test sample compared with the control value identifies the compound as being able to inhibit Wza-mediated polysaccharide transport in the bacteria. An increase or no change in the transport measured in the test sample compared with the control value identifies the compound as not being able to inhibit Wza-mediated polysaccharide transport in the bacteria. The control value is typically obtained separately from the screening method of the invention. For instance, the control value may be obtained beforehand and recorded, for instance on a computer. The control value is used for comparison purposes in the screening method of the invention. The control value may be used for multiple repetitions of the screening method of the invention. The control value is preferably obtained under the same conditions, such as type of assay, concentration of stain, bacterial cell number and bacterial cell type, under which the method of screening is carried out. A person skilled in the art can prepare a suitable control value.

The screening method may comprise (a) providing a test sample of the bacteria and a control sample of the bacteria, (b) contacting the test sample, but not the control sample with the compound; (c) measuring Wza-mediated polysaccharide transport in the test and control samples; and (d) comparing the transport measured in the test sample with the transport measured in the control sample and thereby determining whether or not the compound inhibits Wza-mediated polysaccharide transport in the bacteria. A decreased transport in the test sample compared with the control sample identifies the compound as being able to inhibit Wza-mediated polysaccharide transport in the bacteria. An increase or no change in the transport measured in the test sample compared with the control sample identifies the compound as not being able to inhibit Wza-mediated polysaccharide transport in the bacteria. This method avoids the problems of obtaining the control value separately from the method of the invention. The control sample is preferably handled under the same conditions, such as type of assay, concentration of stain, bacterial cell number and bacterial cell type, under which the test sample is handled. A person skilled in the art can prepare a suitable control sample.

The screening methods may be carried out using any number of different compounds. The screening methods may be carried out using any number of samples. For instance, the methods may be carried out using 1, 2, 5, 10, 15, 20, 30, 40, 50, 100, 150, 200 or more samples. The method is preferably carried out using 96 or 384 test samples using a standard 96 or 384 well plate.

Any number of bacterial cells may be present in the samples. The bacteria in each sample may be incubated with the compound in any volume, for any length of time and at any temperature. Typical volumes of the samples range from about 0.1 µl to about 1 ml, preferably from about 0.2 µl to about 500 µl, more preferably from about 1 µl to about 200 µl, such as about 0.2, about 0.6, about 1.0, about 3.0 or about 5.0 µl. Typically, the length of time for which the cells are incubated with the compound is from about 5 minutes to about 50 hours, for example from about 10 minutes to about 40 hours, from about 20 minutes to about 30 hours, from about 30 minutes to about 20 hours, from about 45 minutes to about 10 hours, such as about 20, about 40, about 60, about 90, about 120 or about 150 minutes or about 3, about 4, about 5, about 6, about 7, about 8, about 9 or about 10 hours. The suitable temperature is typically in the same range as the normal body temperature of the subject which will be infected by the bacteria. Typically, the incubation is carried out at a fixed temperature between about 4° C. and about 38° C., preferably from about 20° C. to about 25° C., more preferably at 20° C.

Any concentration of compound may be used, such as from 1 nM to 10 mM, preferably from 20 µM to 1 mM.

Wza-mediated polysaccharide transport can be measured in any way. Suitable methods are known in the art. Transport is typically measured by the staining of capsular polysaccharide (CPS) and/or lipopolysaccharide (LPS). This can be done by phenol extraction of the CPS and/or LPS followed by carbohydrate staining [1967, Orskov, Eur. J. Biochem.; 1980, Stirm, J. Bacteriol.]. Another approach involves immunoprecipitation with CPS antibody [2000, Whitfield, EMBO J.]. The former staining assay is preferred because it only requires several hours. Glycoprotein stain kits, such as Pro-Q Emerald 300 (Molecular Probes), are commercially available. Transport can also be measured by measuring the current flowing through pores formed from Wza. A compound that interferes or blocks current flow through Wza pores is typically capable of inhibiting Wza-mediated polysaccharide transport.

The invention also describes compounds identified using the screening methods described herein. These compounds may be used in any of the compositions, methods or uses described above.

EXAMPLES

Example 1: Wt-Wza Conductance in Planar Lipid Bilayers

The Wt Wza transporter was tested in single-channel recording, in accordance with the procedures of Naismith (Nature 2006, 444, 226-229) for its ability to form pores in planar lipid bilayers. Sequential insertions of channels in a single orientation were used to measure the conductance of a single channel because more than one channel could insert simultaneously during the first introduction, especially when protein molecules have not properly diffused yet. Repetition of experiments helped to verify conductance of a single channel. FIG. 1a shows a recording of stepwise insertion at +100 mV. FIG. 1(b) shows the histogram of multi-insertion in (a), showing the stepwise increase of current. FIG. 1(c) shows the distribution of open current of wt Wza. After collection of 37 insertions of wt Wza channel, the current of a single channel of wt Wza in 2 M KCl buffer was determined to be 1.89±0.01 pA (n=37) on average, corresponding to 18.9±0.1 pS (n=37) in conductance.

Example 2: Mutant Wza Transporters

The Wza pore was opened by replacing the tyrosines at position 110 that line the narrowest region of the lumen with glycine. To confirm that the currents observed indeed arose from the mutant pore, a cysteine was introduced in the α-helix barrel (Y110G/K375C) and would therefore yield a characteristic reversible blockade when derivatized with a suitable thiol-specific reagent.

The unitary conductance of the Y110G/K375C pore was determined as for wt-Wza, by measuring stepwise-insertion using the same technique referenced above. The mean open current of Y110G/K375C was determined to be +85±14.1 pA (+50 mV, n=31), corresponding to 1.70±0.28 nS (+50 mV, n=31) in conductance.

Example 3: Screening for Blockers

Thirteen commercial cyclodextrins (CDs) were tested for their ability to block WT-Wza and the mutant Y110G/K375C (Table 1) including, neutral, negatively charged or positively charged cyclodextrins. Testing was carried out using electrical channel recording in high salt buffer (2M KCl, 5 mM HEPES, 100 μM EDTA, 200 μM DTT) at pH 7.5. Three cyclodextrins were found to block Wza wt or mutant channels at low voltages (<10 mV) under these conditions. These compounds are the positively charged cyclodextrins $am_6αCD$, $am_7βCD$ and $am_8γCD$, with $K_d$ values of 0.86±0.38 M (n=3), 2.9±1.8 mM (+3 mV) and 12.3±3 μM (+3 mV) respectively at +3 mV. Further single-channel recording of $am_8γCD$ in physiological-close conditions (300 mM KCl, 5 mM HEPES, pH 7.5) revealed that this cyclodextrin bound tightly with Wza channels at low voltages, +5/+10 mV (Table 2).

TABLE 1

Screening of blockers against wt-Wza or Wza Y110G/K375C[a]

| No. | Compound | Interaction with WT Wza | Interaction with mutant Wza |
|---|---|---|---|
| 1 | hexa-6-sulfato-α-cyclodextrin ($S_6αCD$) | not observed | not observed[b] |
| 2 | α-cyclodextrin | not observed | not observed[b] |
| 3 | hexakis (6-amino-6-deoxy)-α-cyclodextrin ($am_6αCD$) | not observed | $K_d$ = 0.86 ± 0.38M (+3 mV, n = 3)[b] |
| 4 | heptakis (6-amino-6-deoxy)-β-cyclodextrin ($am_7βCD$) | $K_d$ = 13 ± 7 mM (+75 mV, n = 3) | $K_d$ = 2.1 ± 0.5 mM (+75 mV, n = 3) $K_d$ = 2.9 ± 1.8 mM (+3 mV, n = 3)[b] |
| 5 | heptakis-6-carboxymethyl-β-cyclodextrin | not observed | not observed[b] |
| 6 | heptakis(2,3,6-tri-O-methyl)-β-cyclodextrin | not observed | not observed[b] |
| 7 | β-cyclodextrin | not observed | not observed[b] |
| 8 | 6-O-(p-toluenesulfonyl)-β-cyclodextrin | poor solubility | not observed[b] |
| 9 | sulfated β-cyclodextrin | $K_d$ > 10 mM (−150 mV) | $K_d$ > 10 mM (−150 mV) |
| 10 | γ-cyclodextrin | not observed | not observed[b] |
| 11 | Octacis-6-carboxymethyl-γ-cyclodextrin | not observed | not observed[b] |
| 12 | Octacis (6-amino-6-deoxy)-γ-cyclodextrin ($am_8γCD$) | not observed | $K_d$ = 12 ± 3 μM (+3 mV, n = 3)[b] |
| 13 | Octacis-6-phosphate-γ-cyclodextrin | not observed | not observed[c] |

[a]The buffer used throughout was 2M KCl, 5 mM HEPES, 100 μM EDTA, 200 μM DTT, pH 7.5.

TABLE 2

Dissociation constants ($K_d$) of $am_8γCD$ with mutant Wza pores in high and low salt buffers.

| | Buffer | | | | | | |
|---|---|---|---|---|---|---|---|
| | 2M KCl (buffered with 5 mM HEPES, 100 μM EDTA, 200 μM DTT, pH 7.5) | | | | | 300 mM KCl (buffered with 5 mM HEPES, pH 7.5) | |
| Mutant | Y110G/K375C | ΔP106-A107 | Y110G | Y110G/Y373C | Y110G/E369C | ΔP106-A107 | Y110G |
| $K_d$ | 12 ± 3 μM (+3 mV, n = 3) | 7.8 ± 5.2 μM (+3 mV, n = 3) | 4.7 ± 4.6 μM (+3 mV, n = 3) | 0.57 ± 0.52 mM (+3 mV, n = 3) | N/A (+3 mV, n = 3) | 44 ± 25 nM (+5 mV, n = 3) | 5.6 ± 2.4 nM (+10 mV, n = 3) | am$_7$βCD and am$_8$γCD elicited clear current blockades. am$_8$γCD binds much more strongly than am$_7$βCD, 10 times or more strongly at different voltages.

Example 4: Inhibition of K30 Polysaccharide Transport Through Wza

The inhibitory effect of am$_8$γCD, am$_7$βCD and am$_6$αCD were tested on live bacteria (*E. coli* strain E69) with K30 capsular polysaccharide (CPS) and Wza as its transporter. Isolation and staining of the polysaccharides was used. Phenol extraction was carried out in accordance with Orskov (Eur. J. Biochem.; 1980, Stirm, J. Bacteriol. 1967) to isolate the capsular polysaccharide (CPS) and lipopolysaccharide (LPS), followed by carbohydrate staining Pro-Q Emerald 300 glycoprotein stain kit (Molecular Probes) was used for staining of both the CPS and LPS. The staining time, loading volume, oxidation time and washing time after staining were optimised and the following conditions used in the assay:
Staining time: 1 hour
Loading volume: 3 μL of the stock aqueous polysaccharide solution (see below), mixed with 3 μL of the Laemmli sample buffer (1 mL, Bio-Rad) mixed with 2-mercaptoethanol (950 microliter:50 microliter) before use;
Oxidation time: 30 minutes
Washing time None Further details of the microbiology and the staining procedures used are as follows: The strains were grown in the absence of or the presence of various concentrations of am$_8$γCD overnight in M9 minimal medium until OD reached ~0.5. Cells were collected by centrifugation of the culture at 2583×g for 20 minutes at 4° C. In the phenol extraction, volume of phenol/buffer (20 mM Tris.-HCl, 2 mM MgCl$_2$, 20 mM NaCl, pH 8.0) to each tube with a cell pellet is calculated as OD*667 μL. Phenol/buffer (1:1) extraction of the cells was performed in a Thermomixer (Eppendorf, No. 5355 31077) at 65° C. and 200 rpm for 10 min, followed by centrifugation at 25,000×g at 4° C. for 20 min. Then the upper aqueous polysaccharide solution was separated and stored at −80° C. for further use. In this way the volumes for phenol/buffer extraction were normalized. By doing this, the cell concentration in each sample was identical so that the changes in CPS and LPS quantity of each cell on average could be compared quantitatively.

The results are depicted in FIG. 2, in which Lane 1 is a marker; lane 2 is a control with no CD; lane 3 is 1 nM am$_8$γCD; lane 4 is 1 μM am$_8$γCD; lane 5 is 1 mM am$_8$γCD; lane 6 is 1 nM am$_7$βCD; lane 7 is 1 μM am$_7$βCD; lane 8 is 1 mM am$_7$βCD; lane 9 is 1 nM am$_6$αCD; lane 10 is 1 μM am$_6$αCD; and lane 11 is 1 mM am$_6$αCD. The inhibition of K30 polysaccharide transport was much stronger by 1 mM am$_8$γCD than that of am$_7$βCD and am$_6$αCD at the same concentration, which agrees with the single-channel recording result that am$_8$γCD has stronger effect than am$_7$βCD on blocking the channels of Wza mutants, with $K_d$ values 12±3 μM (n=3) and 2.9±1.8 mM (n=3) as measured with mutant Y110G/K375C at +3 mV in 2 M KCl, buffered with 5 mM HEPES, 100 μM EDTA, 200 μM DTT, pH 7.5.

Detailed measurement of the inhibitory effect of am$_8$γCD towards K30 polysaccharide translocation was then performed. An aqueous extract of the cells was subjected to SDS-PAGE. The gel was stained to generate fluorescence signals that correspond to the sugar quantity. The results are shown in FIG. 3a, in which CPS (solid line) ~180 kDa; LPS (dash line) ~35 kDa for control and ~45 kDa for other samples. In FIG. 3a Lane 1 is the fluorescent protein marker provided in the staining kit used, Lanes 2 to 12 show different concentrations of am$_8$γCD, with lanes 2 to 12 respectively showing 0, 20, 40, 60, 80, 100, 120, 150, 200, 300 and 1000 micromolar am$_8$γCD. With the increase of am$_8$γCD concentration (0, 20 μM to 1 mM), the K30 CPS amount decreases dramatically and the molecular weight did not change (~180 kDa, FIG. 2), very close to the reported 150 kDa (Eur. J. Biochem. 1967, 2, 115-126).

The fluorescent intensities of the gels were measured by using the Bio-Rad Universal Hood II. The stain has an excitation maximum at ~280 nm and an emission maximum at ~530 nm. The fluorescence intensity of each lane was processed with the Plot Lane function after illumination of the gel with UV light at 302 nm and fluorescent data collection emissions going through an Amber Filter (548-630 nm).

Figure 3B:
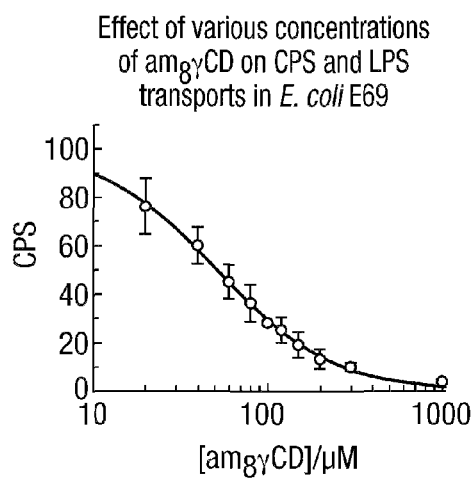
FIGS. 3b and 3c provide the same results plotted on a graph of [$am_8\gamma CD$] vs capsular polysaccharide (CPS) fluorescent intensity (FIG. 3b) and lipopolysaccharide (LPS) fluorescent intensity (FIG. 3c).
Figure 3C:
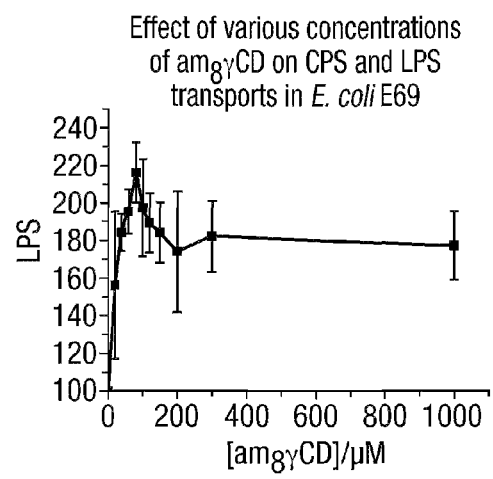

The half maximal inhibitory concentration of am$_8$γCD (IC$_{50}$) could be calculated via the concentration dependence of the CPS band. FIG. 3b shows a plot of the CPS intensity versus the concentration of am$_8$γCD processed with GraFit 7.0, which gave an IC$_{50}$ of 51.2±1.0 μM (n=4). Interestingly, the LPS increased with the decrease of CPS or the increase of am$_8$γCD but stayed saturated at around 2 times that of the control (FIG. 3c).

Example 5: LPS Exposure Assay, Measurement of Exposure of O9a LPS to O9a LPS-Specific Antibodies The direct effect of the inhibition of K30 CPS transport on *E. coli* strain E69 is the appearance of defects in the capsule layer. This should in turn lead to exposure of O9a LPS at the cell surface. To test this hypothesis, the attachment of rabbit anti-O9a antibodies was quantified by flow cytometry (FACS), by using secondary fluorescent anti-rabbit antibodies. The design of the experiment is depicted schematically in FIG. 4a.

*E. coli* strains E69 and CWG281 were grown as described above in Example 4 and the OD$_{600}$ was adjusted to 0.4. The concentrations of cyclodextrin (either am$_8$γCD (compound 13), am$_6$αCD (compound 3) or am$_7$βCD (compound 10)) present in the growth media were 10 nM, 100 nM, 1 μM, 10 μM, 50 μM, 100 μM and 1 mM. 50 μL samples of each were centrifuged at 3,000×g for 10 min to remove the medium, washed with PBS and resuspended in 50 μL PBS. O9a antiserum (0.5 μL) was then added. The mixtures were incubated on ice for 1 h (to compare the effects of am$_6$αCD, am$_7$βCD and am$_8$γCD on the exposure of LPS) or 2 h (for the estimation of minimum effective concentration of am$_8$γCD required to expose LPS to antibodies), followed by centrifugation at 3,000×g for 10 min and washing with PBS. The pellets were resuspended in PBS (50 μL), to which Alexa Fluor 488 Goat Anti-Rabbit IgG secondary antibody (1 μL, Life Technologies, A11034, $\lambda_{ex}$ 495 nm, $\lambda_{em}$ 519 nm) was added, followed by incubation for 1 h on ice. The cells were then centrifuged at 3,000×g for 10 min. The pellets were resuspended in PBS (1 mL), followed by analysis by flow cytometry (FACS) using a Becton-Dickinson FACSCalibur. 10,000 cells were analysed for each sample. Fluorescence was measured in the FL1 channel (530 nm).

Figure 4B:
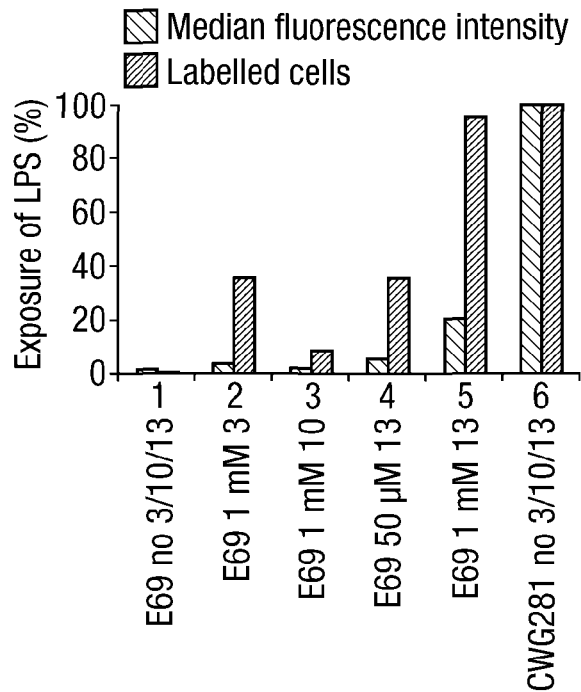
FIGS. 4b and 4c give a comparison of the binding of anti-O9a antibodies to E69 cells cultured with different Wza inhibitors, $am_6\alpha CD$ 3 (1 mM), $am_7\beta CD$ 10 (1 mM) and $am_8\gamma CD$ 13 (50 µM; 1 mM), showing incubation times of 1 hour and 2 hours respectively.

The results are depicted in FIGS. 4b and c. FIG. 4b shows a comparison of the binding of anti-O9a antibodies to E69 cells cultured with different Wza inhibitors, am$_6$αCD 3 (1 mM), am$_7$βCD 10 (1 mM) and am$_8$γCD 13 (50 μM; 1 mM). E69 cells without treatment with inhibitors serve as the negative control, while CWG281 cells, which lack the Wza gene and express no CPS layer, serve as the positive control.

The chart shows the relative median fluorescence intensity of the cells and the percentage of labeled cells in each sample.

FIG. 4b shows the dramatic difference in fluorescence between the untreated E. coli strain E69 and the CPS-minus strain CWG281 which validates this system for measuring LPS exposure. The higher fluorescence intensities of E. coli E69 cells after treatment with 50 μM or 1 mM am$_8$γCD 13 (FIG. 4b, Bar 4.5; 4.9% and 20% by median fluorescence intensity, 36% and 96% by percentage of labelled cells, respectively) by comparison with bacteria treated with 1 mM am$_6$αCD 3 and am$_7$βCD 10 (FIG. 4b, Bar 2.3; 3.2% and 1.8% by median fluorescence intensity; 36% and 9% by percentage of labeled cells, respectively) are consistent with the relative efficacy of these cyclodextrins in electrical recording and carbohydrate staining experiments.

Figure 4C:
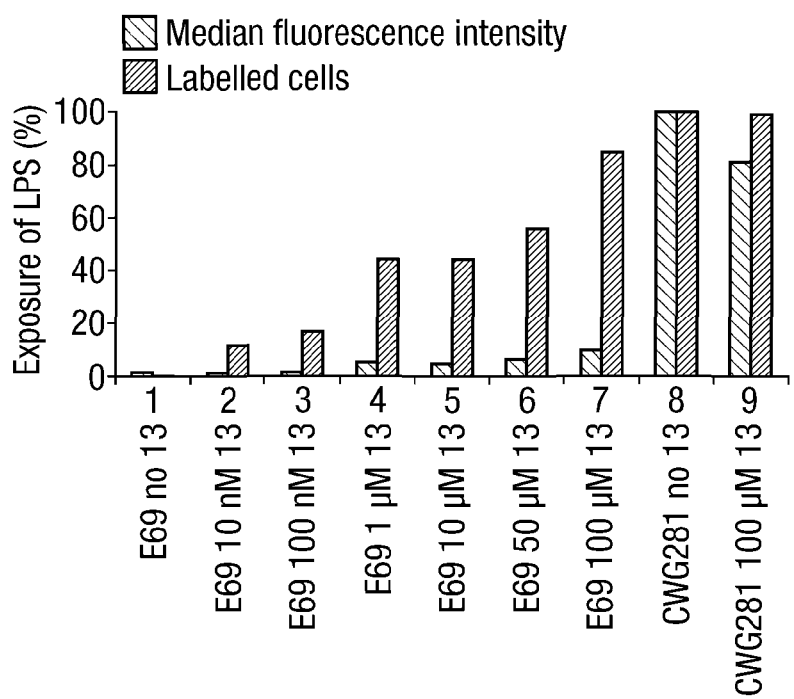

FIG. 4c shows the results of the 2 hour experiment, comparing the binding of anti-O9a antibodies to E69 cells cultured with am$_8$γCD 13 over a range of concentrations: 10 nM 100 nM, 1 μM, 10 μM, 50 μM, 100 μM. E69 cells without treatment with am$_8$γCD 13 serve as the negative control, while CWG281 without treatment with am$_6$αCD 3, am$_7$βCD 10 or am$_8$γCD 13 and CWG281 cultured with 100 μM am$_8$γCD 13 serve as positive controls. The extended experiment time enhances the contrast between the samples. After 2 hours, even at 1 μM, am$_8$γCD 13 caused significant exposure of LPS to LPS-specific antibodies (FIG. 4c, Bar 4; 5.1% by median fluorescence intensity and 44% by percentage of labelled cells).

Example 6: Complement-Mediated Killing of Bacteria

FIG. 5a shows the mode of action of am$_8$γCD 13. Am$_8$γCD 13 inhibits the CPS transport and exposes the LPS to host immune attacks, complement-mediated killing for example.

The exposure of O9a LPS could lead to the binding of antibodies, followed by recognition by the components in the complement, part of the innate immunity, C1q for example. The feasibility of this mechanism was studied in this assay.

This assay measured the killing of bacteria by the compounds of the invention mediated by the human complement system found in serum (incubation time 1 h, RPMI 1640, 37° C.). $10^3$ cells of E. coli strain E69 or CWG281 were cultured in 40% (v/v) normal human serum (NHS, 1 mL, TCS Biosciences, CR100) or deactivated human serum (DHS) in RPMI 1640 medium (Sigma Aldrich, R8758) in 1.5 mL tubes in the presence of different concentrations of am$_8$γCD (compound 13) at 37° C. for 1 h or 4 h. DHS was generated by heating NHS at 56° C. for 30 min. For the one-hour experiment, a portion of each culture (50 μL) was then spread onto a freshly prepared LB-Agar plate; for the four-hour experiment, the culture was firstly diluted 100 times (0, 1, 10, 40 μM), 10 times (100 μM) or not diluted (300 μM and 1 mM), and then a portion of each resulting culture (50 μL) was then spread onto a freshly prepared LB-Agar plate. The plates were incubated at 37° C. for 10 h after which colonies were counted. The total colonies of each sample were calculated by colonies/plate multiplying by times of dilution. P values were calculated from a one-tailed Student's t-test.

Results are shown in FIG. 5b which shows survival of strains E69 (Bars 1-13) and CWG281 (Bars 14-15) in the presence of normal human serum (NHS) or deactivated human serum (DHS). Representative LB-Agar plates corresponding to bars 1, 2, 11, 14 and 15 are shown. Error bars show the means±SD of at least three independent experiments. Normal human serum (NHS) with active complement led to only 15% killing of E69 cells (FIG. 5b, bar 2). Consistent with the feasibility of a mechanism based on increased vulnerability when lacking CPS (FIG. 5a) a genetically-engineered CPS-minus strain (CWG281) in the presence of normal human serum (NHS), in contrast showed no survival, 100% killing.

Killing of bacteria that had been treated with compound am$_8$γCD 13 was then tested. There was no distinct enhancement of complement-mediated killing of E69 until the concentration of am$_8$γCD 13 reached 15 μM (21% killing). Consistent with the proposed mode of action of am$_8$γCD 13, a clear dose response was observed (FIG. 5b, bars 3-11); further increases in the concentration of am$_8$γCD 13 led to more dramatic killing after 1 h, e.g. 51% at 100 μM and 84% at 1 mM. am$_8$γCD 13 alone at 100 μM or 1 mM had no significant effect on the survival of E69 in the absence of NHS, implying that killing was complement-mediated and initiated by the ability of am$_8$γCD 13 to weaken the CPS barrier (FIG. 5b, bars 12, 13). Deactivated human serum (DHS) with ineffective complement showed 0% killing (FIG. 5b, bar 1). Defective CPS layers can only be generated when cells are dividing in the presence of a CPS inhibitor am$_8$γCD 13.

It was therefore hypothesized that an increased incubation time with an inhibitor could lead to more dramatic killing. This was confirmed by increasing the incubation time to 4 h, the results of which are shown in FIG. 5c. In this case, 1 mM am$_8$γCD 13 completely inhibited the growth of E69 (FIG. 5c). The concentration of am$_8$γCD 13 required to kill half of the bacteria (EC$_{50}$) under these conditions was 3.2±0.5 μM (P<0.006, n=3).

The invention claimed is:

1. A method of removing or reducing the thickness of the capsular polysaccharide layer of a bacterium containing the Wza protein, said method comprising contacting the bacterium with a compound that is a cyclic oligosaccharide of Formula (I) or a pharmaceutically acceptable salt thereof, or a mixture of two or more said compounds:

(I)

wherein:
  n is 3; and
  each S is the same or different and represents a saccharide unit, wherein one or more S units is modified at the primary carbon position by replacement of the hydroxyl group with a functional group X which is positively charged, or which bears a positive charge when in aqueous solution at pH 7, wherein each group X is the same or different and represents a group of formula (II):

(II)

wherein:
  p, q and r independently represent 0 or 1;
  Alk$_1$ represents a straight or branched C$_{1-6}$ alkylene group wherein one or more of the CH$_2$ groups is optionally replaced with a heterogroup selected from —O—, —S—, —NR—, —NRCO—, —CONR, —CO—, —OCO— and —COO—, and wherein one or more of the $CH_2$ groups is optionally substituted with a substituent selected from OR, SR, NRR', $CH_2OR$, $CH_2SR$ and $CH_2NRR'$, wherein R and R' independently represent H or a $C_{1-2}$ alkyl group;

Ar represents phenyl;

$Alk_2$ represents methylene or ethylene; and

A represents $—NR_2$ or

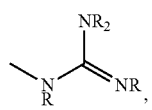

wherein each R is the same or different and represents H or a $C_{1-2}$ alkyl group, and wherein A may be in the form of a free base or may be protonated to form a cation;

wherein the method is an in vivo method for removing or reducing the thickness of the capsular polysaccharide layer of a bacterium in a subject, and wherein the contacting is carried out by administering, orally or parenterally, to said subject an effective amount of said compound that is a cyclic oligosaccharide of Formula (I) or pharmaceutically acceptable salt thereof, or said mixture of two or more said compounds.

2. The method of claim 1, further comprising contacting the bacterium with another antibacterial or antimicrobial agent.

3. The method according to claim 1, wherein the compound or the mixture of two or more compounds is the only active agent administered to said subject.

4. The method according to claim 1, wherein the compound is a cyclodextrin of Formula (IA) or a pharmaceutically acceptable salt thereof:

(IA)

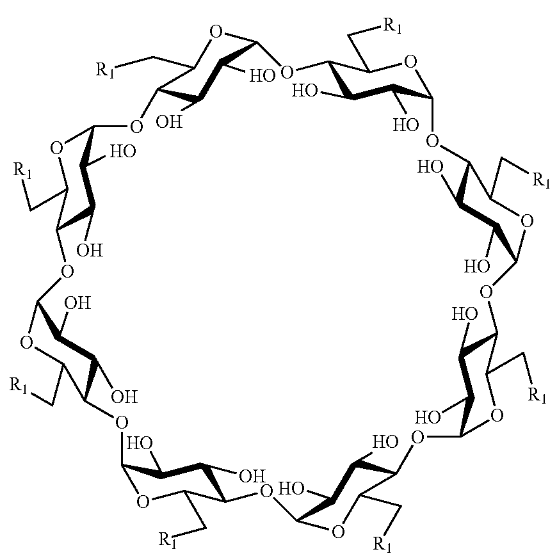

wherein each $R_1$ is the same or different and is selected from OH or a group X, wherein at least 6 $R_1$ groups represent a group X, and wherein each group X is the same or different and represents a functional group which is positively charged, or which bears a positive charge when in aqueous solution at pH 7.

5. The method according to claim 4, wherein X is $NH_2$.

6. The method according to claim 1, wherein removing or reducing the thickness of the capsular polysaccharide layer of the bacterium results in the antigens on the bacteria being attacked by the subject's immune system.

7. The method according to claim 1, wherein removing or reducing the thickness of the capsular polysaccharide layer of the bacterium results in the killing of the bacterium in the subject.

8. The method according to claim 1, wherein removing or reducing the thickness of the capsular polysaccharide layer of the bacterium inhibits the growth of the bacterium in the subject.

9. The method according to claim 1, wherein the bacterium is other than *Staphylococcus aureus*.

10. The method according to claim 1, wherein the bacterium is selected from *Acinetobacter Venetianus, Eschericia coli, Klebsiella pneumonia, Achtinobacillus suis* or *Bordetella bronchiseptica*.

11. A method of removing or reducing the thickness of the capsular polysaccharide layer of a Wza-containing bacterium in a subject, said method comprising administering to said subject, orally or parenterally, an effective amount of a compound that is a cyclic oligosaccharide of Formula (I) or pharmaceutically acceptable salt thereof, or a mixture of two or more said compounds:

(I)

wherein:

n is 3; and each S is the same or different and represents a saccharide unit, wherein one or more S units is modified at the primary carbon position by replacement of the hydroxyl group with a functional group X which is positively charged, or which bears a positive charge when in aqueous solution at pH 7, wherein each group X is the same or different and represents a group of formula (II):

$$-(Alk_1)_p-(Ar)_q-(Alk_2)_r-A \quad (II)$$

wherein:

p, q and r independently represent 0 or 1, $Alk_1$ represents a straight or branched $C_{1-6}$ alkylene group wherein one or more of the $CH_2$ groups is optionally replaced with a heterogroup selected from —O—, —S—, —NR—, —NRCO—, —CONR, —CO—, —OCO— and —COO—, and wherein one or more of the $CH_2$ groups is optionally substituted with a substituent selected from OR, SR, NRR', $CH_2OR$, $CH_2SR$ and $CH_2NRR'$, wherein R and R' independently represent H or a $C_{1-2}$ alkyl group;

Ar represents phenyl;

$Alk_2$ represents methylene or ethylene; and

A represents $—NR_2$ or wherein each R is the same or different and represents H or a $C_{1-2}$ alkyl group, and wherein A may be in the form of a free base or may be protonated to form a cation;

wherein removing or reducing the thickness of the capsular polysaccharide layer of the bacterium inhibits the growth of the bacterium in the subject.

* * * * *